United States Patent
Burg et al.

(10) Patent No.: US 9,607,380 B2
(45) Date of Patent: *Mar. 28, 2017

(54) METHODS AND APPARATUS FOR QUANTIFYING COLOR CHANGES INDUCED BY SPECIFIC CONCENTRATIONS OF BIOLOGICAL ANALYTES

(71) Applicant: SCANADU INCORPORATED, Moffett Field, CA (US)

(72) Inventors: Bernard Burg, Menlo Park, CA (US); Martin Zizi, Enines (BE); Aaron Alexander Rowe, San Francisco, CA (US); Anthony Smart, Costa Mesa, CA (US); Walter De Brouwer, Los Altos, CA (US)

(73) Assignee: Scanadu Incorporated, Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/081,884

(22) Filed: Mar. 26, 2016

(65) Prior Publication Data

US 2016/0260215 A1 Sep. 8, 2016

Related U.S. Application Data

(63) Continuation of application No. 14/419,939, filed as application No. PCT/US2013/035397 on Apr. 5, 2013, now Pat. No. 9,311,520.

(Continued)

(51) Int. Cl.
*G01J 3/46* (2006.01)
*G06T 7/00* (2006.01)

(Continued)

(52) U.S. Cl.
CPC .......... *G06T 7/0014* (2013.01); *A61B 5/1172* (2013.01); *G01N 21/27* (2013.01);

(Continued)

(58) Field of Classification Search
CPC ........ G01J 3/46; G01J 3/50; G01J 3/51; G01J 3/02; G01J 3/524

(Continued)

(56) References Cited

U.S. PATENT DOCUMENTS 9,311,520 B2 * 4/2016 Burg ................ G01N 35/00029

\* cited by examiner

*Primary Examiner* — Abdullahi Nur
(74) *Attorney, Agent, or Firm* — Alford Law Group, Inc.

(57) ABSTRACT

Methods and electronic devices for performing color-based reaction testing of biological materials. The method includes capturing and interpreting digital images of an unexposed and later exposed paddle at various delay times within an automatically calibrated environment. The test paddle includes a unique identification mechanism (UID), a Reference Color Bar (RCB) providing samples of standardized colors for image color calibration, compensation and corrections, and several test-specific sequences of Chemical Test Pads (CTP). The method further includes locating the paddle in the image, extracting the UID and validating the paddle, extracting the RCB and locating the plurality of CTP in each image. The method further reduces image noise in the CTP and calibrates the image automatically according to lighting measurements performed on the RCB. To determine test results, the method further determines several distances between the CTP and its possible trajectory in the color space described by the Manufacturer Interpretation Color Chart.

17 Claims, 20 Drawing Sheets

Related U.S. Application Data

(60) Provisional application No. 61/680,842, filed on Aug. 8, 2012.

(51) Int. Cl.
    *G06K 9/00*       (2006.01)
    *A61B 5/117*      (2016.01)
    *G01N 21/27*      (2006.01)
    *G01N 21/84*      (2006.01)
    *G01N 35/00*      (2006.01)
    *G06T 7/40*       (2006.01)
    *G01N 21/78*      (2006.01)
    *G06T 7/60*       (2006.01)
    *G01J 3/02*       (2006.01)
    *G01N 21/17*      (2006.01)

(52) U.S. Cl.
CPC .......... *G01N 21/274* (2013.01); *G01N 21/78* (2013.01); *G01N 21/8483* (2013.01); *G01N 35/00029* (2013.01); *G06K 9/00046* (2013.01); *G06T 7/004* (2013.01); *G06T 7/408* (2013.01); *G06T 7/60* (2013.01); *G01J 3/02* (2013.01); *G01J 3/46* (2013.01); *G01N 2021/1765* (2013.01); *G01N 2021/8488* (2013.01); *G01N 2035/00108* (2013.01); *G01N 2201/12* (2013.01); *G06T 2207/10024* (2013.01); *G06T 2207/30004* (2013.01)

(58) Field of Classification Search
USPC ................................................ 356/402–425
See application file for complete search history.

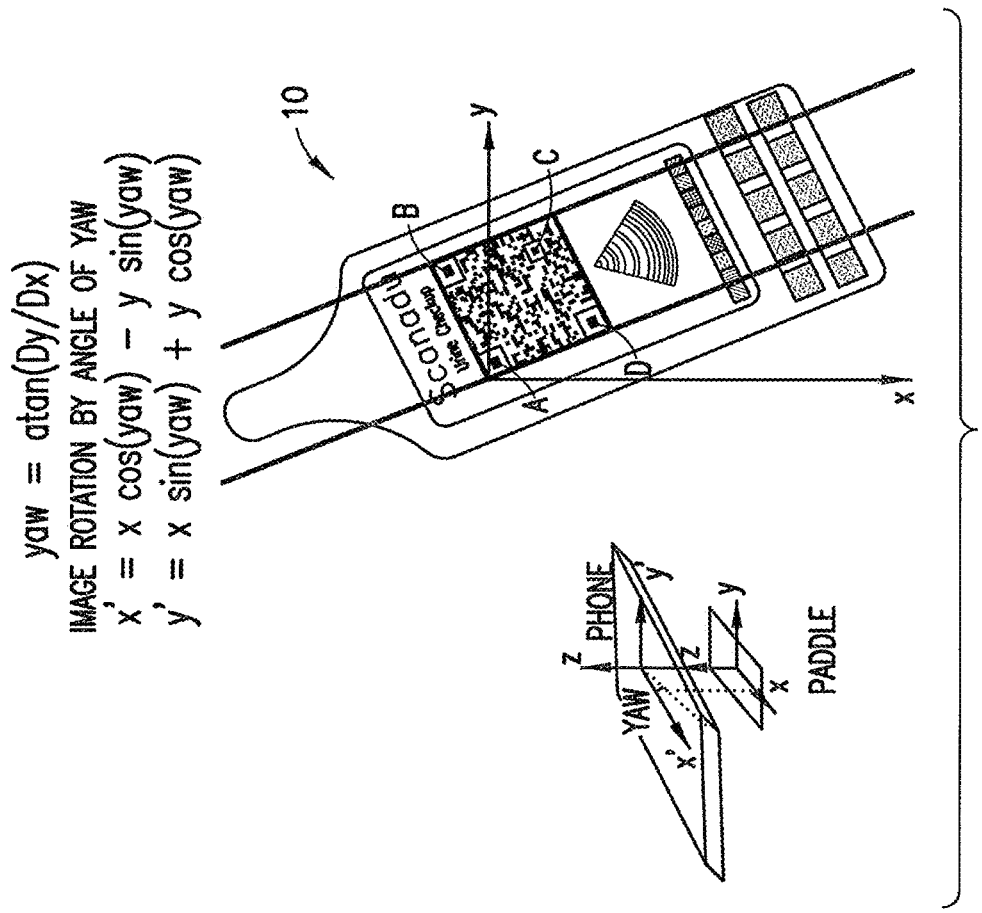
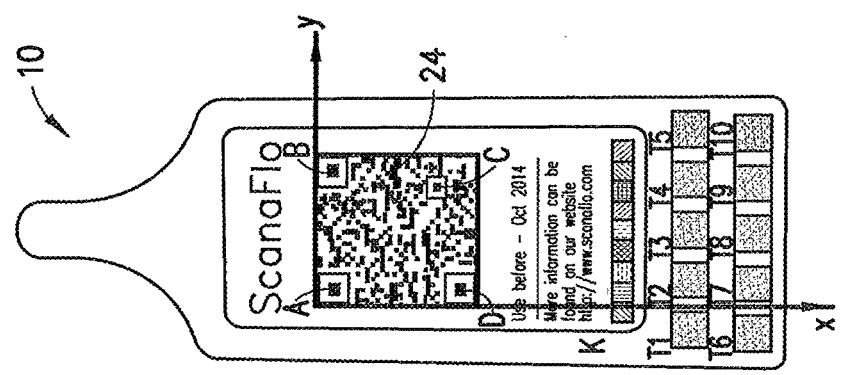
FIG. 6B
FIG. 6A

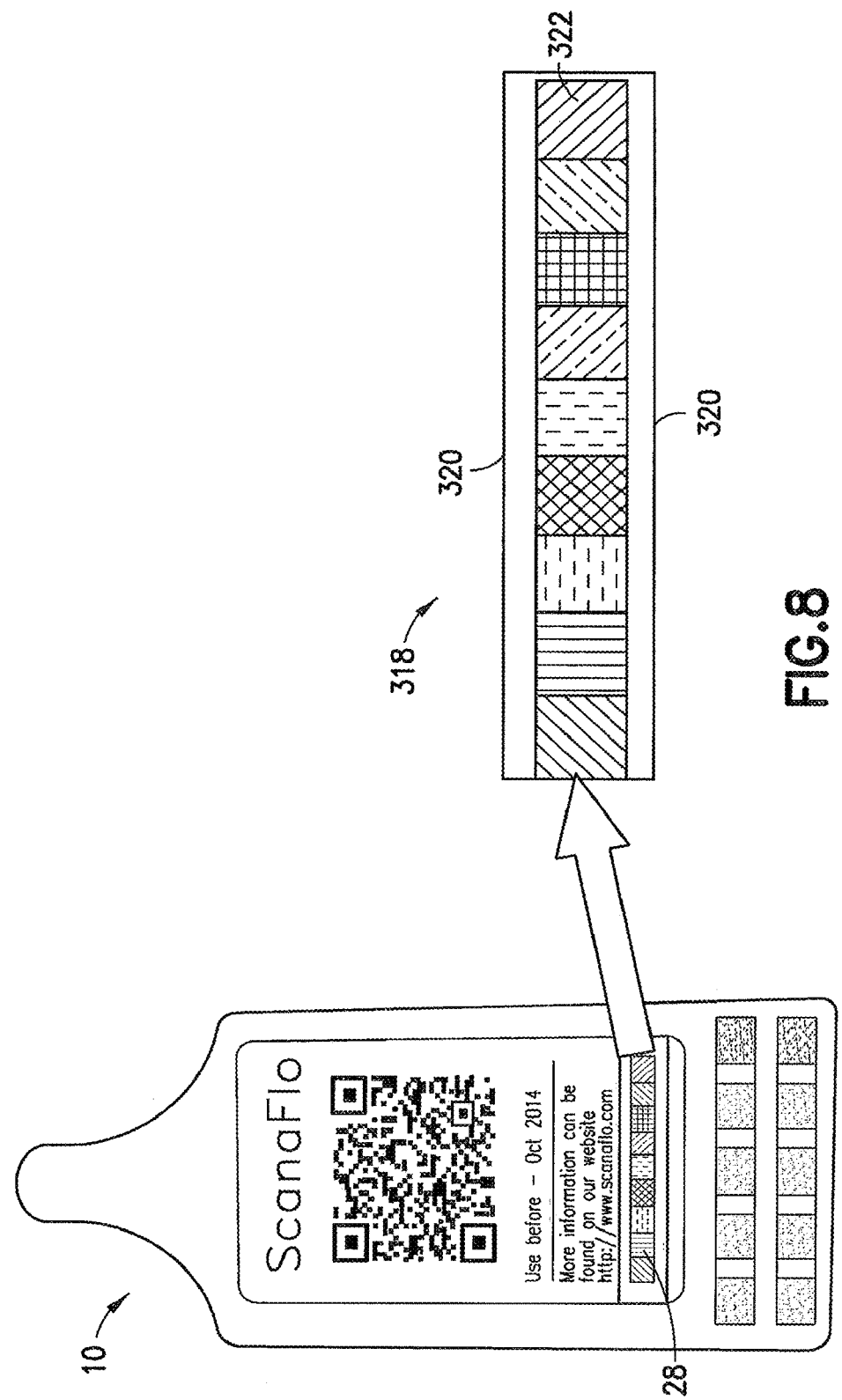

FIG. 14

URINE LEUCOCYTES

Q : [Urine are cloudy ?/unusual smell ?]

| Possible causes | Prompted Questions | Associated readings |
|---|---|---|
| Urinary tract Infection | | |
| Bladder | [frequent needs to urinate] | [blood, sometimes] [nitrites] |
| Kidney | [if high fever] | [blood] [nitrites] |
| Inflammation | | [Proteins] |
| Pregnancy | [pregnant] | |
| Sexual activity | [new partner] | |
| | [increase in activity] | |
| Physical damage | | |
| To Kidney | [antecedents of stones] | [Proteins] [blood] [creatinine] |
| | [known kidney disease] | |
| To prostate | [known prostatic problems] | [Proteins] [blood] |
| Physical anomaly | [kidney duplication,...] | |
| False positive | [poor sample collection] | |

FIG. 15

URINARY PROTEINS

Q: [Urine foamy?]
   [Transient?]
   [Permanent? More than 2 readings a few weeks apart]

*IF TRANSIENT:*

| Possible causes | Prompted Questions | Associated readings |
|---|---|---|
| High fever | [Fever] | |
| Extreme temperatures | [external temp] [Physical activity] | |
| Sport activities | [Increased physical activity] [Extreme physical activity] | [Blood, Hemoglobin++] |
| Stress ++ | [Stress or unusual event] | |

*IF PERMANENT:*

| Possible causes | Prompted Questions | Associated readings |
|---|---|---|
| Urinary tract infection | | |
|   Bladder | [frequent needs to urinate] | [blood, sometimes] [nitrites] [leucocytes] |
|   Kidney | [if high fever] | [blood] [nitrites] [leucocytes] |
| High Blood pressure | [BP] | [blood traces, sometimes] |
| Kidney diseases | | |
|   Stones | [antecedents of stones] [known kidney disease] | [Proteins] [blood] [creatinine] |
| Consecutive to Systemic (see below) | | |
| Heart problems | [heart condition, ...] | |
| Pre-eclampsia | [pregnancy] [high blood pressure] [sudden weight gain/ water retention] | [blood] |
| Diabetes (advanced) | [known?, duration?, insulin or not?] [vascular problems] [difficulty to march] [loss of sensitivity: hands, feet,...] | [sugar] [blood] [creatinine] |
| Drugs side effects | [intake of antibiotics] [intake of aminoglycosides (names)] [altered hearing] [recent use of painkiller] [intake of phenazone derivatives (names)] | [creatinine] |
| Systemic diseases | [known SD] [high blood pressure, sometimes] | [blood, sometimes] [creatinine] [bilirubine] [leucocytes] | ex of SD: Rheumatoid arthritis, Hodgkin lymphoma, multiple myeloma...

METHODS AND APPARATUS FOR QUANTIFYING COLOR CHANGES INDUCED BY SPECIFIC CONCENTRATIONS OF BIOLOGICAL ANALYTES

CROSS REFERENCE TO RELATED APPLICATIONS

This application claims the benefit of U.S. patent application Ser. No. 14/419,939 entitled METHOD AND APPARATUS FOR PERFORMING AND QUANTIFYING COLOR CHANGES INDUCED BY SPECIFIC CONCENTRATIONS OF BIOLOGICAL ANALYTES IN AN AUTOMATICALLY CALIBRATED ENVIRONMENT filed Feb. 6, 2015. U.S. patent application Ser. No. 14/419,939 claims the benefit of Patent Cooperation Treaty (PCT) Application No. PCT/US2013/035397 entitled METHOD AND APPARATUS FOR PERFORMING AND QUANTIFYING COLOR CHANGES INDUCED BY SPECIFIC CONCENTRATIONS OF BIOLOGICAL ANALYTES IN AN AUTOMATICALLY CALIBRATED ENVIRONMENT filed Apr. 5, 2013. Application No. PCT/US2013/035397 claims the benefit of U.S. Provisional Patent Application No. 61/680,842 entitled MULTI-ANALYTE RAPID DIAGNOSTIC TEST AND METHOD OF USE filed Aug. 8, 2012, which is hereby incorporated by reference in its entirety.

BACKGROUND OF THE INVENTION

Field of the Invention

The invention relates generally to systems and methods for detecting the presence or absence of a variety of analytes in a fluid sample using a diagnostic instrument, and, in particular, for determining diagnostic test results by image analysis of a digital image of the diagnostic instrument.

Description of Related Art

Reagent dipsticks and immunoassays have been used in medical clinics for decades in connection with methods for rapidly diagnosing health conditions at the point of care. In a clinical environment, dipsticks have been used for the diagnosis of urinary tract infections, preeclampsia, proteinuria, dehydration, diabetes, internal bleeding and liver problems. As is known, dipsticks are laminated sheets of paper containing reagents that change color when exposed to an analyte solution. Each reagent test pad on the dipstick is chemically treated with a compound that is known to change color in the presence of particular reactants. For example in the context of urinalysis, the dipstick will typically include reagent pads for detecting or measuring analytes present in a biological sample such as urine, including glucose, bilirubin, ketones, specific gravity, blood, pH, protein, urobilirubin, nitrite, leukocytes, microalbumin and creatinin.

The magnitude of this color change is proportional to analyte concentration in the patient fluid. Dipsticks are typically interpreted with the naked eye by comparing the test strip against a colored reference chart. However, such color comparison can cause user confusion and error, for several reasons including changes in ambient lighting, and that a significant portion of the population has impaired color vision.

Automatic methods and apparatus for interpreting test results of dipsticks and immunoassays, which have been exposed to a sample solution, are known in the art. For example, U.S. Patent Application Publication No. 2012/0063652 to Chen et. al (hereinafter "the '652 publication") discloses a method for color-based reaction testing of biological materials, albeit in an un-calibrated environment, by capturing a digital image of both a test strip and a colored reference chart side by side in a single image. The test results for the test strip are automatically obtained by performing simple color matching between the reacted regions of the test strip and the color reference chart to determine analyte concentration of the biological material.

When employing the method disclosed by the '652 publication, a user must properly align the test strip and the color reference chart before capturing the digital image. Therefore, a user must come into contact with the exposed test strip, after it is soiled by biological samples, such as urine, blood, or feces, and place it in an appropriate position relative to the color reference chart. Therefore, to assist in placement of the test strip and/or chart, automatic interpretation apparatus often include an additional positioning element, such as a box or carpet, to position both the test strips and the chart in the correct orientation.

In view of the problems with presentably available methods for automatically reading test strips, there is a need for an automated testing method, which uses a digital image captured in an un-calibrated environment. The system or method should be configured to automatically calibrate the digital image to correct any color deficiencies, artifacts, or other ambiguities. The method should also automatically identify the relevant portions of the digital image, regardless of how the test strip and/or color reference are positioned in the digital image. Finally, the method should minimize manipulation of samples soiled with biological fluids. The presently invented method and system address these deficiencies of known automatic detection devices, systems, and methods.

SUMMARY OF THE INVENTION

Generally provided are a method and electronic user device for performing quantitative assessment of color changes induced by exposure of multiple test strips to a biological material/fluid. Preferably, the provided system and method permits automatic calibration of a digital image of a plurality of test media which have been exposed to a sample solution, for the purpose of determining whether certain analytes are present or absent from the sample solution. More preferably, the invention provides a method and electronic user device to quantify color changes induced in various test strips by exposure to the sample. This quantification is based on an automatic calibrating protocol, independent of variations in the external environment. This invention yields accurate, precise, and cost effective measurements while minimizing the user interaction with biological samples. This method is designed to support medical scientific instruments complying with FDA and EU regulations in the field aimed at minimizing errors.

Therefore according a preferred and non-limiting embodiment of the invention, a computer-implemented method for quantifying color change of at least one test medium on a diagnostic instrument is provided. The method includes the step of capturing a digital image of at least a portion of the diagnostic instrument, which has been exposed to a biological sample. The diagnostic instrument includes at least one color reference comprising a plurality of reference samples of different colors and at least one test medium containing a reagent, which changes color in the presence of particular analytes in the biological sample. The method further includes the following steps: identifying at least one of the reference samples for the at least one medium in the diagnostic instrument; determining a dominant camera-captured color of a reference sample and a dominant camera-captured color of the at least one test medium; color correcting the dominant camera-captured color of the at least one test medium based on a correction factor derived at least in part from the dominant camera-captured color of the reference sample to determine a corrected test medium color; and comparing the corrected test medium color to a set of possible test medium colors corresponding to predetermined analyte concentrations to determine a test result including an analyte concentration of the biological sample being tested.

In accordance with a further embodiment of the present invention, a computer-implemented method for determining a relative position on a diagnostic instrument includes the step of capturing a digital image of at least a portion of the diagnostic instrument, which has been exposed to a biological sample. The diagnostic instrument includes at least one test medium containing a reagent, which changes color in the presence of particular analytes in the biological sample. The method further includes the following steps: scanning the digital image to identify the position of a predetermined region on the diagnostic instrument; identifying the at least one test medium on the digital image based at least in part on the position of the predetermined region; and determining a test result by comparing the color of the at least one test medium to a set of possible test medium colors corresponding to predetermined analyte concentrations to determine an analyte concentration of the biological sample being tested.

In accordance with a further embodiment of the present invention, a method for validating a diagnostic instrument includes the step of capturing a pre-use digital image of at least a portion of the diagnostic instrument, prior to exposing the diagnostic instrument to a biological sample. The diagnostic instrument includes at least one color reference comprising a plurality of reference samples of different colors and at least one test medium containing a reagent, which changes color in the presence of particular analytes in the biological sample. The method further includes the following steps: identifying the at least one test medium in the pre-use digital image of the diagnostic instrument; comparing a color of the at least one test medium to a set of possible test medium colors for reagents, which have not been exposed to an analyte; and determining whether the diagnostic instrument is in condition for use based at least in part on the color of the at least one test medium.

In accordance with a further embodiment of the invention, a diagnostic instrument for identifying a plurality of test results by testing a single patient fluid is provided. The instrument includes: an instrument housing; a color reference comprising a plurality of reference samples of different colors affixed to or associated with the housing for determining the test results from a digital image of the diagnostic instrument; and a plurality of test media affixed to the housing containing color-changing reagents, which change color in the presence of particular analytes in a biological sample.

In accordance with a further embodiment of the invention, a system for reading diagnostic test results is provided. The system includes a diagnostic instrument and a portable electronic device having a camera sensor for capturing a digital image of at least a portion of the diagnostic instrument and a processor. The diagnostic instrument includes a color reference having a plurality of reference samples of different colors and a plurality of test media containing reagents, which change color in the presence of particular analytes in the biological sample. The processor of the portable electronic device is configured to: identify at least one of the reference samples and at least one of the test media on the digital image of the diagnostic instrument; determine a dominant camera-captured color of a reference sample and a dominant camera-captured color of at least one test medium; color correct the dominant camera-captured color of the at least one test medium based on a correction factor derived at least in part from the dominant camera-captured color of the reference sample to determine a corrected test medium color; and compare the corrected test medium color to a set of possible test medium colors corresponding to predetermined analyte concentrations to determine a test result including an analyte concentration of the biological sample being tested.

In accordance with a further embodiment of the invention, a portable electronic device for analyzing a digital image of a diagnostic instrument is provided. The diagnostic instrument includes at least one color reference having a plurality of reference samples of different colors and at least one test medium containing a reagent, which changes color in the presence of particular analytes in the biological sample. The portable electronic device includes: at least one processor; at least one display device; at least one camera sensor (digital image capture device); and at least one computer-readable medium including program instructions. When executed by the at least one processor, the programming instructions cause the portable electronic device to: capture a digital image of at least a portion of the diagnostic instrument, which has been exposed to a biological sample, with the camera sensor; identify at least one of the reference samples for the at least one medium in the diagnostic instrument; determine a dominant camera-captured color of a reference sample and a dominant camera-captured color of the at least one test medium; color correct the dominant camera-captured color of the at least one test medium based on a correction factor derived at least in part from the dominant camera-captured color of the reference sample to determine a corrected test medium color; and compare the corrected test medium color to a set of possible test medium colors corresponding to predetermined analyte concentrations to determine a test result including an analyte concentration of the biological sample being tested.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and the claims, the singular form of "a", "an", and "the" include plural referents unless the context clearly dictates otherwise.

BRIEF DESCRIPTION OF THE DRAWINGS

For the purpose of facilitating understanding of the invention, the accompanying drawings and description illustrate preferred embodiments thereof, from which the invention, various embodiments of its structures, construction and method of operation, and many advantages may be understood and appreciated.

FIGS. 6A-6D are photographic representations of a diagnostic instrument with markings to indicate the orientation of the instrument in the photograph relative to the x-axis, the y-axis, or the z-axis.

FIG. 8 is a magnified photographic representation of a reference color bar as identified by the geometric correction calculations, of the method of FIG. 4.

FIG. 14 is one embodiment of a decision tree for identifying patient conditions related to increased urine leukocytes, according to the principles of the invention.

FIG. 15 is one embodiment of a decision tree for identifying a patient condition related to an increase in urinary proteins, according to the principles of the invention.

DESCRIPTION OF THE PREFERRED EMBODIMENTS

Figure 1:
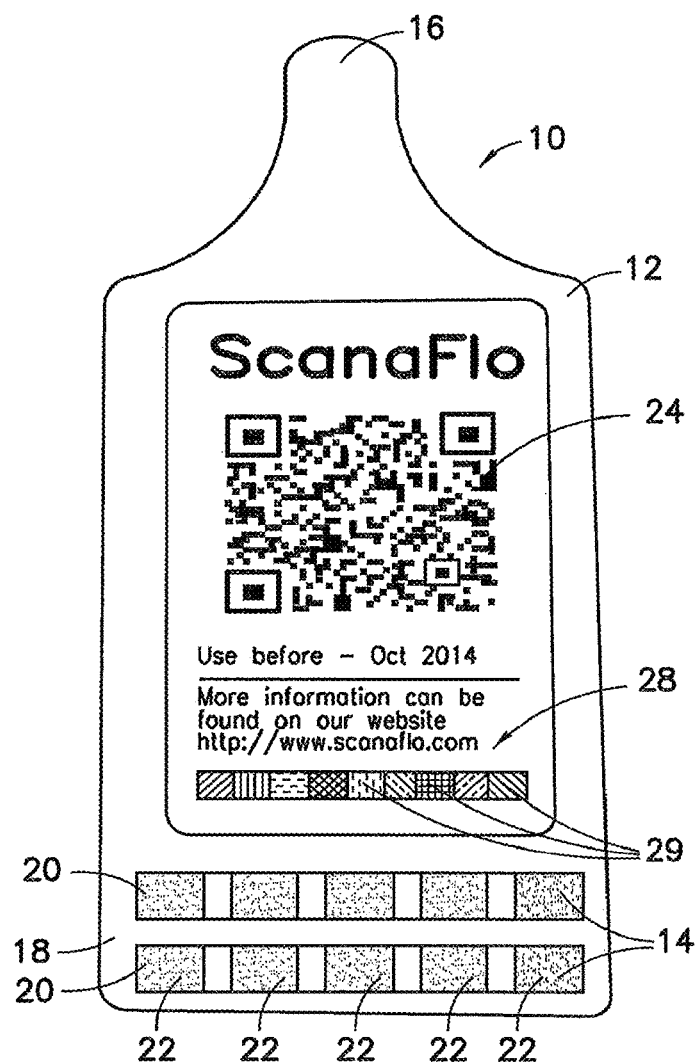
FIG. 1 is a top view of one embodiment of a diagnostic instrument, according to the principles of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

As used herein, the terms "communication" and "communicate" refer to the receipt or transfer of one or more signals, messages, commands, or other type of data. For one unit or component to be in communication with another unit or component means that the one unit or component is able to directly or indirectly receive data from and/or transmit data to the other unit or component. This can refer to a direct or indirect connection that may be wired and/or wireless in nature. Additionally, two units or components may be in communication with each other even though the data transmitted may be modified, processed, and/or routed between the first and second unit or component. For example, a first unit may be in communication with a second unit, even though the first unit passively receives data, and does not actively transmit data to the second unit. As another example, a first unit may be in communication with a second unit if an intermediary unit processes data from one unit and transmits processed data to the second unit. It will be appreciated that numerous other arrangements are possible. The components or units may be directly connected to each other or may be connected through one or more other devices or components. The various coupling components for the devices can include but are not limited to, the Internet, a wireless network, a conventional wire cable, an optical cable or connection through air, water or any other medium that conducts signals, and any other coupling device or medium.

The present invention is drawn to diagnostic instruments, systems and methods of use thereof for testing of a patient fluid sample, which can be used either in clinical settings or for home use. More particularly, the invention relates to the performance of color-based reaction testing of biological material in an automatically calibrated environment. The preferred embodiment of the invention is implemented as an application running on a portable electronic device, such as a cell phone, tablet PC, computer, laptop, or other dedicated electronic device. The method has been designed to minimize user contact and manipulations of biologically soiled samples. Error prevention and compliance with medical instrument regulations have been implemented at all levels in the design of protocols. In particular the invented methods have been designed avoid modifying, compromising, and discarding raw data.

The diagnostic instrument is configured to provide rapid detection of patient conditions using test strips, such as reagent dipsticks. Dipsticks are typically narrow strips of plastic or paper having certain reagents or antibodies that act as recognition elements to detect a given analyte or disease marker in a patient fluid sample. Often, the intensity of a color change of the test strip is an indication of the concentration of the analyte or disease marker in the patient fluid. Patient fluid may include a urine sample, blood sample, patient cells disposed in a fluid solution (e.g. cells obtained from a throat swab), semen, mucous, blood, saliva, and the like.

The diagnostic instrument is configured to test a patient fluid sample for a variety of diseases and patient conditions to increase the likelihood that a variety of conditions may be identified during a testing activity. Thus, the user will not need to select which test to perform or the order in which tests should be performed. In one non-limiting preferred embodiment, the diagnostic instrument may test for pregnancy and pregnancy complications, such as preeclampsia.

With reference to FIG. 1, and in one preferred and non-limiting embodiment, provided is a diagnostic instrument 10, including a paddle 12 for holding at least one test strip 14. The paddle 12 includes a handle 16 and a testing region 18 adapted to hold a plurality of test strips 14. The testing region 18 includes a plurality of indentations 20 for holding at least one individual test strip 14. The test strip 14 may be a reagent dipstick. In that case, each test strip 14 includes a plurality of test media, such as Chemical Test Pads (CTP) 22, containing a color-changing reagent for identifying the concentration of certain analytes in a patient fluid, such as urine, blood, or saliva. The user exposes the diagnostic instrument 10, including the test strips 14, to the fluid sample by dipping the instrument 10 into the patient fluid sample to submerge the test strips 14. As is shown in FIG. 1, more than one test strip 14 can be affixed to the paddle 12, thus increasing the number of analytes that can be tested. In certain embodiments, the paddle 12 allows for testing of a number of analytes simultaneously.

A diagnostic instrument 10 which allows a user to test a single fluid sample for a variety of patient conditions is intended to reduce user anxiety and to inspire confidence in individuals without medical training and with limited experience in performing medical tests. More particularly, the diagnostic instrument 10 tests for a plurality of patient conditions, meaning that the user does not need to select an appropriate test or determine which conditions are most likely to be present. Instead, in a single testing activity, the user tests for a plurality of conditions using a single fluid sample exposed to a single diagnostic instrument 10. Furthermore, the diagnostic instrument 10 includes the paddle 12 and the handle 16, making the diagnostic instrument 10 easies for a user to maneuver. Similarly, the handle 16 ensures that the user is protected from contacting the fluid sample during the test. Therefore, a user may confidently perform the test, using the diagnostic instrument 10, without worrying that he or she will accidently contact patient fluid. Additionally, the diagnostic instrument 10 is intended to be provided with clear and easy-to-understand instructions for performing the test and interpreting the results, to ensure that the untrained user receive accurate diagnostic information from the tests that are being performed.

With continued reference to FIG. 1, the diagnostic instrument further includes a color reference, such as a Reference Color Bar (RCB) 28, disposed on the diagnostic instrument 10. The RCB 28 includes a plurality of color samples 29 in a side-by-side linear arrangement. For example, the RCB 28 may include color samples 29 for one or more of the following colors: Cyan, Magenta, Yellow, Key (black), Gray, White, Red, Green, Blue. The color sample 29 colors correspond with common colorspaces, such as Red-Green-Blue or Cyan-Magenta-Yellow-Key (black). The RCB 28 is used for image processing, specifically to calibrate a digital image of the diagnostic instrument 10 to improve the quality and accuracy of color analysis.

In certain preferred and non-limiting embodiments, the diagnostic instrument 10 further includes an identification label, such as a unique identification (UID) 24. The UID may be a visual indicia serving as a landmark to identify a specific area of the diagnostic instrument. Additionally, the UID 24 may be configured to contain certain identification information about the diagnostic instrument 10, such as a list of the analytes that are being tested, expiration date of the instrument 10, the conditions that are being tested, and other identifying information. The information may be printed directly on or encrypted with the UID 24, such as is the case with a label or two-dimensional bar code, such as a QR code. Alternatively, the UID 24 may be associated with information stored elsewhere, such as is the case with bar codes or other near-field communication codes. The identification information may be used in validation processes to ensure the diagnostic instrument 10 is suitable for the tests being performed and to ensure that it is safe to use, in good working condition, or to resolve other issues which may impact quality and reliability of the test results. It is noted that methods for automatically analyzing test strips in the prior art do not include these steps for validating the diagnostic instrument.

As will be described in greater detail below, the diagnostic instrument 10 is configured so that a digital image of the instrument may be captured using a portable electronic device such as a smart phone. The diagnostic instrument 10 of the present invention is easier to use than diagnostic instruments of the prior art, such as test strips disclosed in the '652 publication. Specifically, unlike previously known systems and methods, a user does not need to handle the used test strips, soiled by biological samples such as urine, blood, feces, etc., because the used diagnostic instrument does not need to be placed in side by side arrangement with an interpretation table, such as a Manufacturer's Interpretation Color Chart (MICC), when obtaining the digital image. Additionally, since the diagnostic instrument 10 does not need to be placed next to corresponding MICC, there is no possibility of using the wrong MICC for a particular diagnostic instrument (e.g. reading strips from manufacturer A with a MICC from manufacturer B).

Having described the structure of an embodiment of the diagnostic instrument 10, a system 100 for reading diagnostic test results using the diagnostic instrument 10 will now be described.

Figure 2:
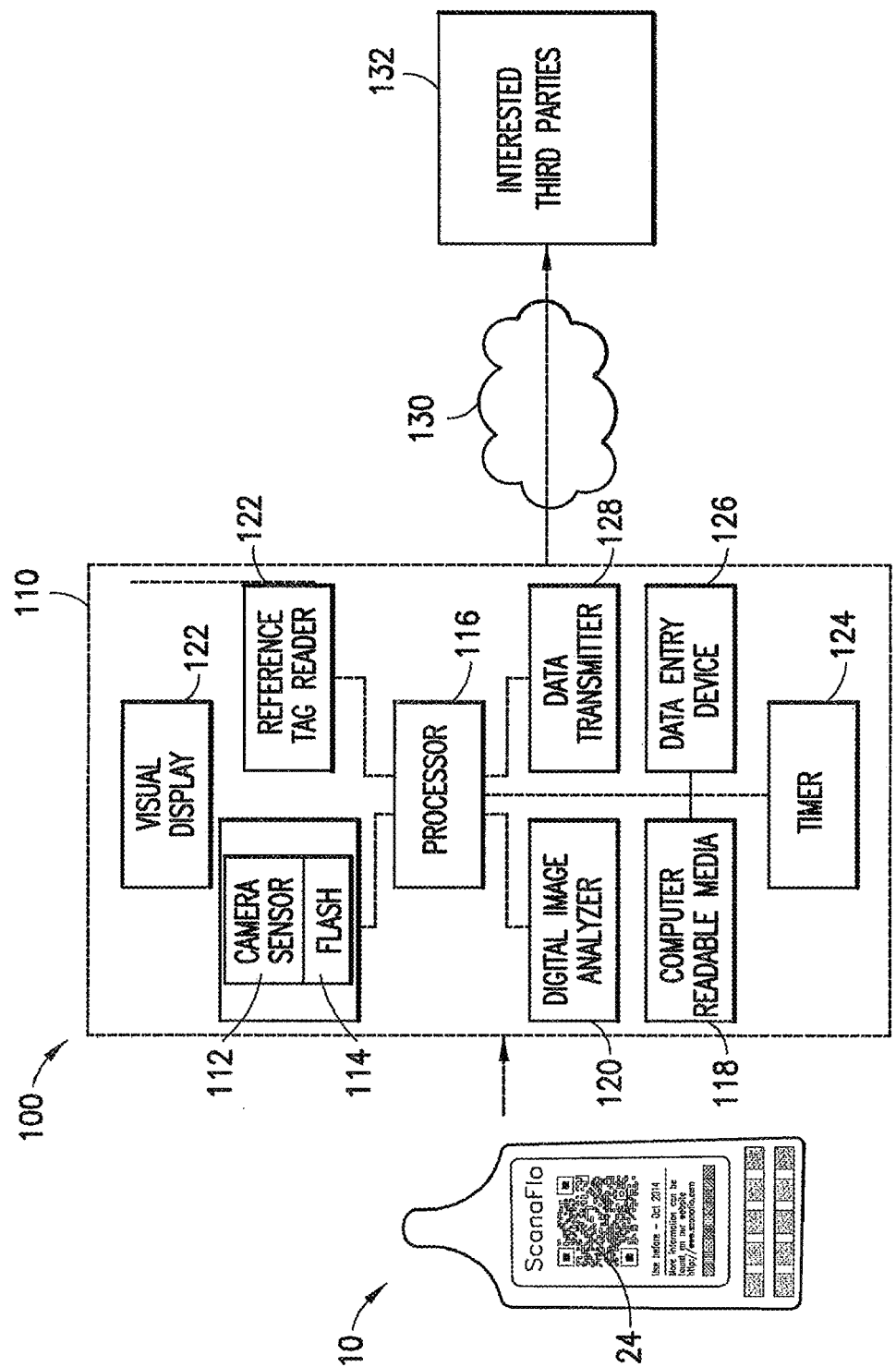
FIG. 2 is a schematic view of one embodiment of a system for analyzing a biological sample using the diagnostic instrument of FIG. 1, according to the principles of the present invention.

With reference to FIG. 2, a system 100 for reading diagnostic test results includes the diagnostic instrument 10 and a portable electronic device 110. Generally, and in various preferred and non-limiting embodiments, the system 100 is used for acquiring, evaluating, analyzing, processing, and/or presenting image data of a diagnostic instrument 10 obtained by the portable electronic device 110. The system 100 may be used in any type of medical analytical/diagnostic setting, including at a medical clinic, at an off-site laboratory, or home use without medical supervision. It should be understood that different aspects of the invention can be appreciated individually, collectively, or in combination with each other. In addition, image data may include any type or form of visual, video, and/or observable data, including, but not limited to, a discrete image, a sequence of images, one or more images from a video, a video sequence, and the like.

The portable electronic device 110 could be any kind of smartphone (e.g., Apple iPhone, BlackBerry), handheld computer (e.g., Apple iPad), or any type of personal computer, network computer, workstation, minicomputer, mainframe or the like running any operating system, such as any version of Android, Linux, Windows, Windows NT, Windows 2000, Windows XP, MacOS, UNIX, Solaris, or iOS.

In certain non-limiting embodiments, the portable electronic device 110 includes a camera sensor 112, for obtaining the digital image of the diagnostic instrument. Certain sensor array chips are presently available with varying properties, with CCD (Charge Coupled Device) and CMOS (Complementary Metal Oxide Conductor) representing the most common camera sensor chips. Each chip technology offers advantages and these evolve relatively with improving designs. In summary, a CCD offers a larger energy capture fraction and serial read-out with minimal local processing, whereas a CMOS has addressability and processing capability for each pixel, but with some loss of sensitivity. The portable electronic device 110 may further include a flash 114 for improving the quality and readability of images captured with the camera sensor 112.

Hereinafter, the system 100 is described in terms of functional components and various processing steps. It is noted that the functional blocks may be realized by any number of hardware and/or software components configured to perform specified functions. In a preferred and non-limiting embodiment, the functional components and processing steps are associated with and/or performed using the portable electronic device 110. For example, the invention may employ various integrated circuit components (e.g., memory elements, processing elements, logic elements, lookup tables, and the like), which may carry out a variety of functions under the control of one or more processors or other control devices. Similarly, the software components of this invention may be implemented with any programming or scripting languages such as C, C#, C++, Java, assembler, extensible markup language (XML), or extensible style sheet transformations (XSLT). The various algorithms may be implemented with any combination of data structures, objects, processes, routines, or other programming elements.

With continued reference to FIG. 2, in one non-limiting embodiment, it is envisioned that the functional components and processing steps will be included with and/or performed using the portable electronic device 110. In that case, the portable electronic device 110 includes a processor 116 configured to execute program instructions stored on computer-readable media 118 associated with the portable electronic device 110. For purposes of the present discussion, computer-readable media 118 may include computer storage media, such as media implemented in any method or technology for storage of information, such as computer-readable instructions, data structures, program modules, or other data, random access memory (RAM), read only memory (ROM), electrically erasable programmable read only memory (EEPROM), flash memory, or other memory technology, CD-ROM, digital versatile disks (DVDs), or other optical disk storage, magnetic cassettes, magnetic tape, magnetic disk storage, or other magnetic storage devices, or any other medium which can be used to store the desired information and which can be accessed by an electronic device, such as portable electronic device 110.

In certain non-limiting embodiments of the program, the processor 116 controls a digital image analyzer 120 for identifying regions of a digital image containing relevant data, color correcting the digital image, and comparing the corrected portions of the digital image to table entries of the MICC to determine test results. The processor 116 may further control a reference tag reader 122 configured to identify and extract information from a UID 24 affixed to or associated with the diagnostic instrument 10. The processor 116 may further control a display 122, connected to or associated with the portable electronic device 110, for presenting information such as instructions for using the diagnostic instrument and test results to a user. The processor 116 may also control a timer 124 for measuring the time between when the diagnostic instrument 10 is exposed to a fluid sample and when the digital image of the diagnostic instrument 10 is captured. Additionally, in certain embodiments, the processor 116 controls a data entry device 126 allowing a user to enter additional information, including patient history information, symptoms, and physical characteristics of the user. The data entry device 126 may include any input device or user interface as is known in the art, which allows a user to control an electronic device including, but not limited to, gestures on a touch-screen or any other actions that cause a change in readings obtained from sensors, keypad presses, and the like.

In addition to storing the program for controlling functions of the portable electronic device 110, the computer-readable media 118 may also store data including a plurality of MICC tables used to determine test results. The computer readable media 118 may also store raw images obtaining by the camera sensor 112, decision trees for determining a patient condition, and other input data necessary for executing functions of the program. Additionally, the computer-readable media 118 may include communications media, such as computer-readable instructions, data structures, program modules, or other data in other transport mechanisms and include any information delivery media, wired media (such as a wired network and a direct-wired connection), and wireless media. Computer-readable media may include all machine-readable media with the sole exception of transitory, propagating signals. Of course, combinations of any of the above should also be included within the scope of computer-readable media.

Additionally, it is to be recognized that some or all of the functions, aspects, features, and instances of the present invention may be implemented on a variety of computing devices and systems, wherein these computing devices include the appropriate processing mechanisms and computer-readable media for storing and executing computer-readable instructions, such as programming instructions, code, and the like. The functional aspects of the App or other software for directing the function of the portable electronic device will be discussed in greater detail below in connection with methods for using the diagnostic instrument to identify a patient condition and methods of image processing of a digital image of the diagnostic instrument.

In a further non-limiting embodiment, the system 100 includes a data transmitter 128 for transmission of data and information from the portable electronic device 110 to an external electronic device, a computer network, and/or a digital storage device, collectively referred to as a network environment 130, known colloquially as "the cloud". Once the data is provided to the network environment 130, it may be made available to interested third parties 132, including caregivers, doctors, third party payment organizations, insurance and health maintenance organizations, pharmacists, or public health organizations.

Having described the diagnostic instrument 10 and a system including the diagnostic instrument 10 and the portable electronic device 110, methods for using the diagnostic instrument and obtaining test results will now be discussed in further detail.

Figure 3:
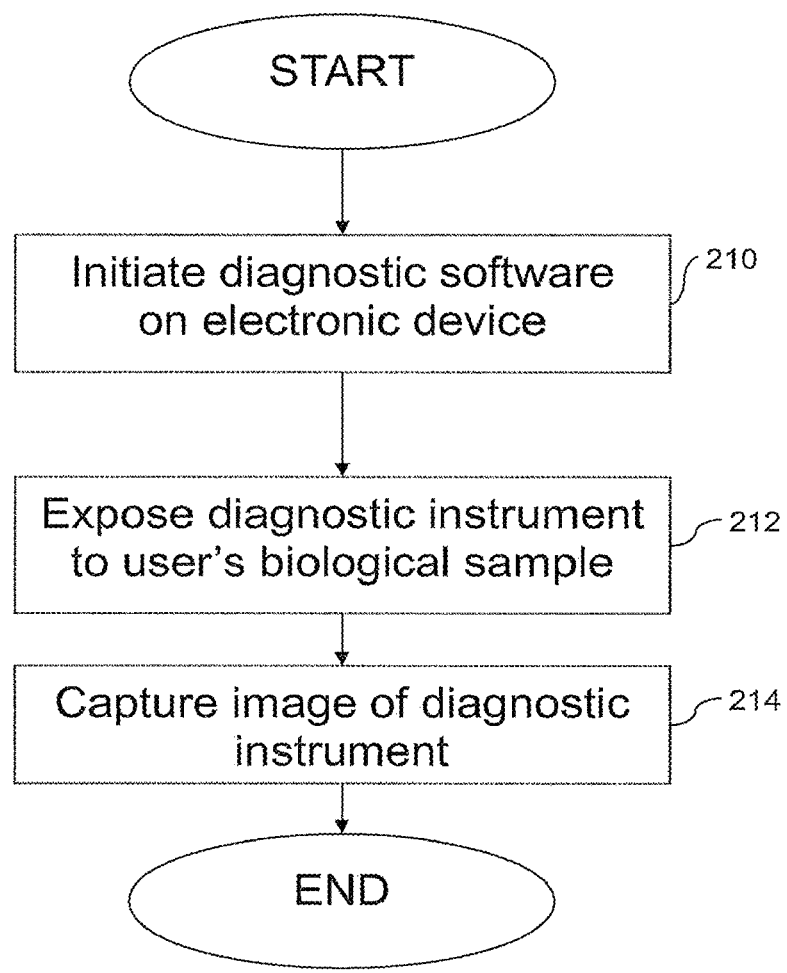
FIG. 3 is a flow chart of an embodiment of a method for capturing an image of a diagnostic instrument.

Initially, as depicted in FIG. 3, a method for obtaining a digital image of the diagnostic instrument is depicted. A user begins by installing the software program configured to acquire and analyze a digital image of the diagnostic instrument on a portable electronic device. Once the software program is installed, the user initiates the program 210, by an active activation means such as by pressing a "Begin" button on the display screen of the portable electronic device. The user then exposes 212 the diagnostic instrument to a biological sample, which exposes the plurality of CTP to analytes contained in the sample and begins a chemical reaction between the CTP and analytes. In certain embodiments, a timer is started when the diagnostic instrument is exposed to the sample. After a predetermined time passes, the portable electronic device prompts the user to capture the digital image of the diagnostic instrument. The timing when the digital image is captured is critical because colors of the CTP continue to change over time. Therefore, missing this acquisition window may void any test results from the diagnostic instrument. Alternatively, additional calculations may be performed to compensate for the incorrect exposure time.

The user captures 214 the digital image of the diagnostic instrument 10 using the camera sensor of the portable electronic device. In certain embodiments, the portable electronic device may provide instructions for obtaining the digital image, such as by suggesting a preferred camera position or lighting environment. For example, in certain embodiments, when preparing to capture the digital image of the diagnostic instrument, the user interface superimposes a virtual contour of the diagnostic instrument onto the real image acquired by the camera sensor in video mode. The user is then asked to overlay the virtual contour with the image of the diagnostic instrument and to take the picture precisely when indicated by the timer. When the user triggers the camera shutter, the camera is configured to switch from video to a high resolution mode to capture a high resolution single frame image of the diagnostic instrument. The captured digital image includes at least a portion of the RCB, the CTP, and/or the UID of the diagnostic instrument. More particularly, a high definition image of the diagnostic instrument is captured preferably under flash or other standardized illumination conditions (if available) so as to provide the most reproducible lighting conditions.

Figure 4:
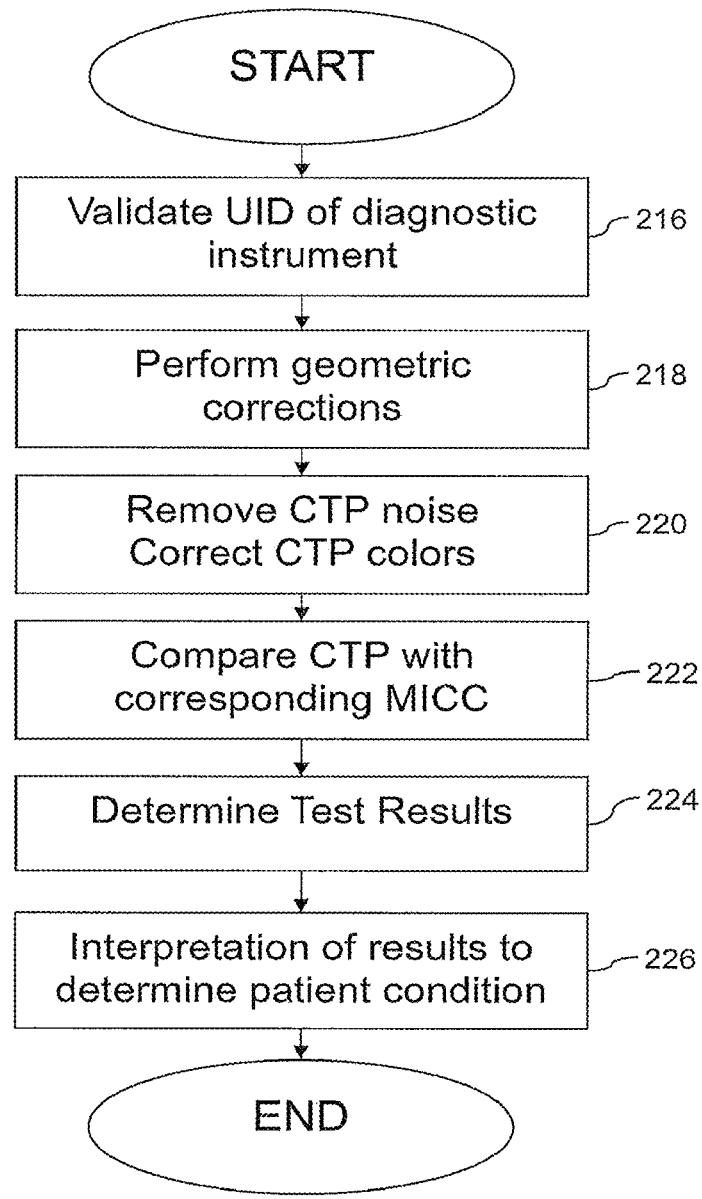
FIG. 4 is a flow chart of an embodiment of a method for determining a patient condition from a digital image of a diagnostic instrument, according to the principles of the present invention.

In certain non-limiting embodiments and with reference to FIG. 4, once the digital image of the diagnostic instrument is obtained, the portable electronic device may be used to validate 216 the diagnostic instrument. Specifically, an optical reader (e.g. bar code, matrix bar code reader, two-dimensional bar code reader, or a QR code reader), associated with the portable electronic device, is used to scan the captured digital image to locate the UID. The UID includes or corresponds to information about the diagnostic instrument being tested. The software is configured to ensure that the diagnostic instrument is safe for use and suitable for a specific application, based on the identification information from the UID. Additionally, the UID validation step may include using the identification information from the UID to select the correct MICC, from available options stored on the portable electronic device, for use in analyzing the results of the diagnostic instrument being tested.

Following the validation step 216, geometric corrections are performed 218 to determine the position of the other elements, namely the RCB and CTP, of the diagnostic instrument based on the position and orientation of the UID. Geometric corrections compensate for a large range of user positioning and attitude errors, which may occur as the user holds the instrument to capture the digital image. The geographic corrections may be defined in terms of pitch, roll, and yaw angles of the diagnostic instrument in the digital image. Based on the geometric correction, the position of the RCB and CTP can be effectively identified. The method further includes applying local image corrections to the identified portions of the digital image including the RCB or CTP, such as analyzing the digital image to apply spatial guard bands around and just within the boundary of each identified area.

With continued reference to FIG. 4, after the digital image is obtained and the geometric corrections performed, the digital image is processed to remove image noise and to correct image coloration 220. It is noted that all of the operations, corrections, calculations, and modifications are performed on a stored copy of the high-definition image. In this way, the raw image is separately maintained and can be used for later analysis, if necessary. More specifically, the color correction process corrects colors of the portion of a copy of the captured image including the CTP, based on the calibration measurements and correction offset determined from analysis of the portion of the digital image including the RCB.

Figure 5:
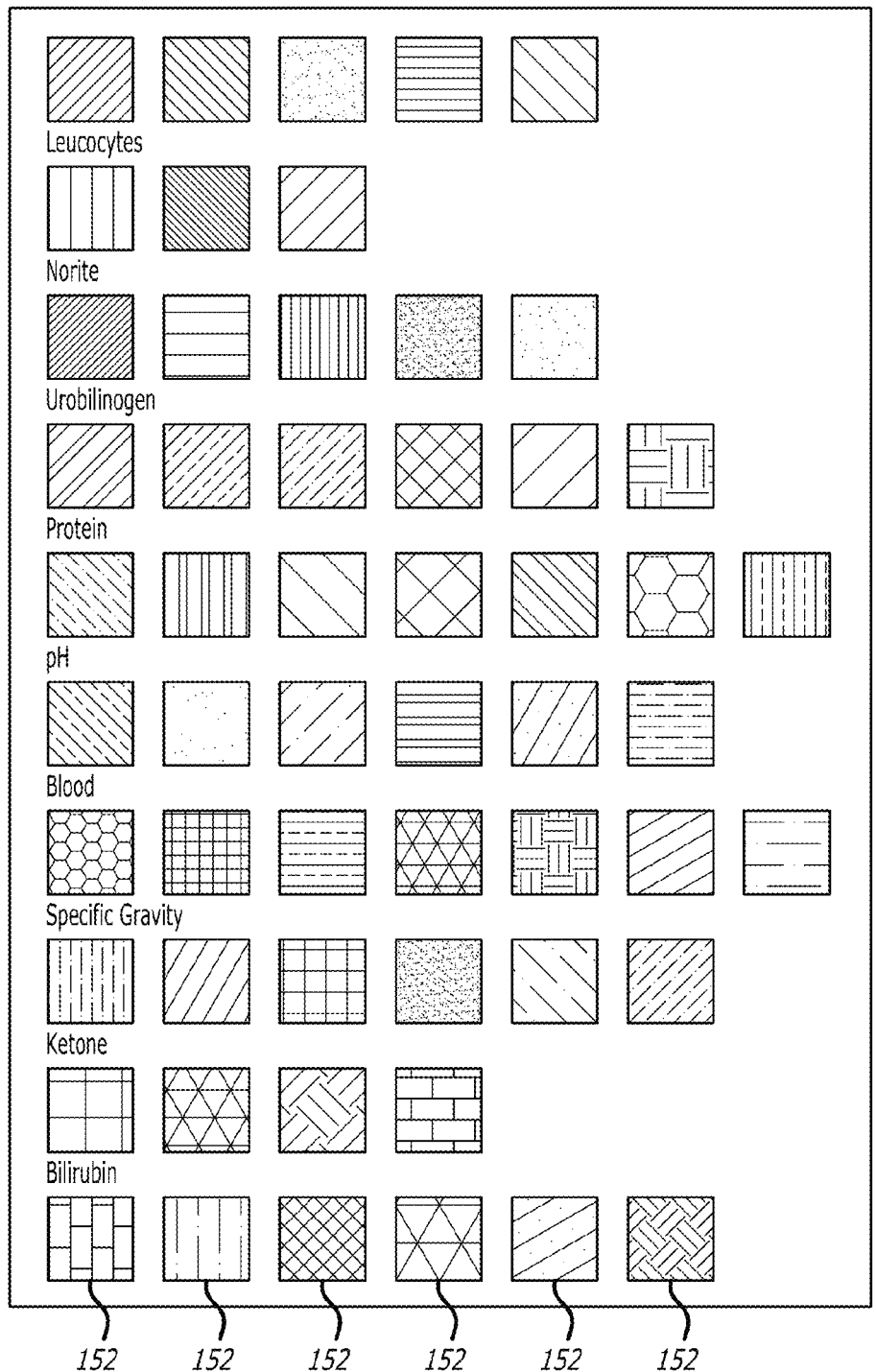
FIG. 5 is a schematic view of a Manufacturing Interpretation Color Chart (MICC) for use in urinalysis, as is known in the prior art.

Once the portions of the digital image including the CTP are color corrected, the corrected colors can be compared 222 with color samples from the MICC. As is described in greater detail below, comparison between the CTP color change and the MICC is based on an interpolation process. The MICC is a table depicting a plurality of possible results (e.g. color samples) for one or more of the CTP on the diagnostic instrument. An exemplary MICC 150 for use with a standard test strip is depicted in FIG. 5. The MICC 150 includes a plurality of color samples 152 corresponding to the range of possible color changes of the CTP being tested. The various color samples correspond to CTP color change over a range of analyte concentrations or titration level (e.g. absent, normal, positive, very positive . . . ). The MICC 150 is typically provided by the manufacturer of the test strip being tested. With continued reference to FIG. 4, based on the comparison between the corrected CTP color and the MICC color samples, the test results (e.g. concentration or titration level) are be determined 224.

In certain embodiments, the predetermined MICC values are also used to provide confirmation that the diagnostic instrument provides valid results and is suitable for use. More particularly, the MICC represents the range of possible color changes for the CTP. If the color of the identified region does not correspond to a possible test result color, it is assumed that either the wrong MICC was used to analyze the test results or that the diagnostic instrument was defective. Accordingly, any results falling outside of the color range defined by the MICC are discarded.

With continued reference to FIG. 4, the test results for an individual CTP can be interpreted 226 either individually or in combination with other test results and diagnostic information to determine a patient condition 226. For example, multiple test results that indicate the presence or absence of a number of different analytes in the fluid sample can be considered in combination to determine a probable patient condition. Similarly, if the test results suggest a number of possible patient conditions, the method may further include asking the patient various diagnostic questions to rule out certain possible conditions to arrive at a most likely patient condition. In certain embodiments, the test results and/or patient condition information are presented to a user on a visual display of the portable electronic device.

Having generally described methods for using the diagnostic instrument, capturing a digital image of the diagnostic instrument, and for determining test results using a portable electronic device, the various processes, algorithms, and methods for analyzing the digital image will now be described in greater detail. It is understood that the processes described below are intended only as exemplary processes and methods for analyzing a digital image of a diagnostic instrument, and are not intended to limit the scope of the present invention in any way. Furthermore, it is understood that the described processes may be implemented using the portable electronic device or other computers and processing apparatus as are known in the art, within the scope of the present invention.

Validation of the Diagnostic Instrument Based on the UID

As shown in FIG. 4, a non-limiting embodiment of the method includes the step of validating 216 the UID to ensure that the diagnostic instrument is suitable for the test being performed. The validation step requires determining the position of the UID on the digital image of the diagnostic instrument. To determine the UID position, the digital image may be scanned using a digital reader or similar image processing algorithm or device. The scanning function may also be used to ensure that the whole diagnostic instrument is acceptably in focus in the digital image. If the digital image is not properly focused, the user may be asked to obtain a replacement image of the diagnostic instrument.

The UID may be implemented as a matrix or two-dimensional bar code, such as a QR code. In other embodiments, the UID is a bar code or near-field communication tag. The UID includes or is associated with certain identifying information about the diagnostic instrument, including the manufacture date of the diagnostic instrument, the expiration date of the diagnostic instrument, the analytes tested for by the instrument, identifying information about the test subject, or patient condition information. For QR codes and similar visual indicia, the identifying information is embedded expressly on the UID itself. The embedded information can be encrypted using various encryption security mechanisms, as are known in the art. Alternatively, the information on the UID may direct the electronic device or digital reader to information stored on an external device. The UID is read according to standard algorithms that are well known in the art. Optionally, the information about the diagnostic instrument contained on the UID may be used to compare the diagnostic instrument with other available testing instruments to ensure that the diagnostic instrument is compatible with software and hardware of the portable electronic device and is the most suitable testing device available for a given application.

Additionally, the validation operation 216 may be used to ensure that the device was legally obtained and was not tampered with during shipping to a user. For example, the UID may contain information about the manufacturer, source, and traceability (e.g. point of origin of the diagnostic instrument and any third parties that have handled the instrument since it was manufactured) of the diagnostic instrument. If any of the identifying information is suspect or incorrect, the diagnostic instrument may be rejected and the user informed that the diagnostic test cannot be performed. Such validation actions prevent rogue and/or unsafe products from being used, such as products that were sold illegally or were acquired from unlicensed third parties.

Perform geometric corrections to identify CTP and RCB

The method further includes performing geometric corrections 218 on the digital image, taking into account the geometric deformations of the initial image to find the proper CTP and RCB sub-images of the CTP and RCB. The process takes into account the geometric deformations of the initial image to find the proper CTP and RCB sub-images, which are subsequently cropped, as precisely as possible, to remove any edge artifacts from the identified regions of the digital image, leaving only the individual colored areas of the CTP and RCB for further analysis.

When preparing to take pictures, the user interface superimposes a virtual contour of the paddle onto the real image acquired by the camera in video mode prior to single frame acquisition in high resolution camera mode. The user is asked to overlay the virtual contour with the image of the paddle and to take the picture precisely when indicated by the timer in this embodiment.

When the user triggers the camera shutter, the camera switches from video to high resolution mode to capture the best possible image of the paddle, improving the precision of the method described in this patent application.

Specifically, the geometric corrections are based on the position of the UID in the digital image. Initially, the position of the UID is identified by scanning the digital image, as is described above in connection with the validation process. With reference to FIGS. 6A-6D, in certain embodiments of the method, four UID 24 points A, B, C, D are identified on the corners of the UID 24 to form a square of known dimensions that encloses the UID 24. Based on the orientation of the UID 24 in the digital image, the vertical (X-scale) and horizontal (Y-scale) scales, as well as, scale factors, including the yaw, pitch, and roll, of the diagnostic instrument 10 are calculated. Based on the calculated position of the UID 24 and scale factors, a theoretic location of the CTP 22 and the RCB 28 can be calculated. The calculated theoretic positions are identified on the digital image. Identification of the CTP and RCB allows for extraction of CTP and RCB sub-images from the digital image of the diagnostic instrument 10. The calculations required to determine the theoretic locations are described herein. Notations used in the following are:

$$A(x,y)=Ax, Ay$$

$$Ti(x,y)=Tix, Tiy$$

With reference to FIG. 6B, the yaw angle (rotation around Z axis) is directly measured in the image by:

$$yawAngle=a\tan((Ay-Dy)/(Ax-Dx))$$

and the positions are corrected through a rotation around point A, creating a new referential X' and Y'.

Figures 6C, 6D:
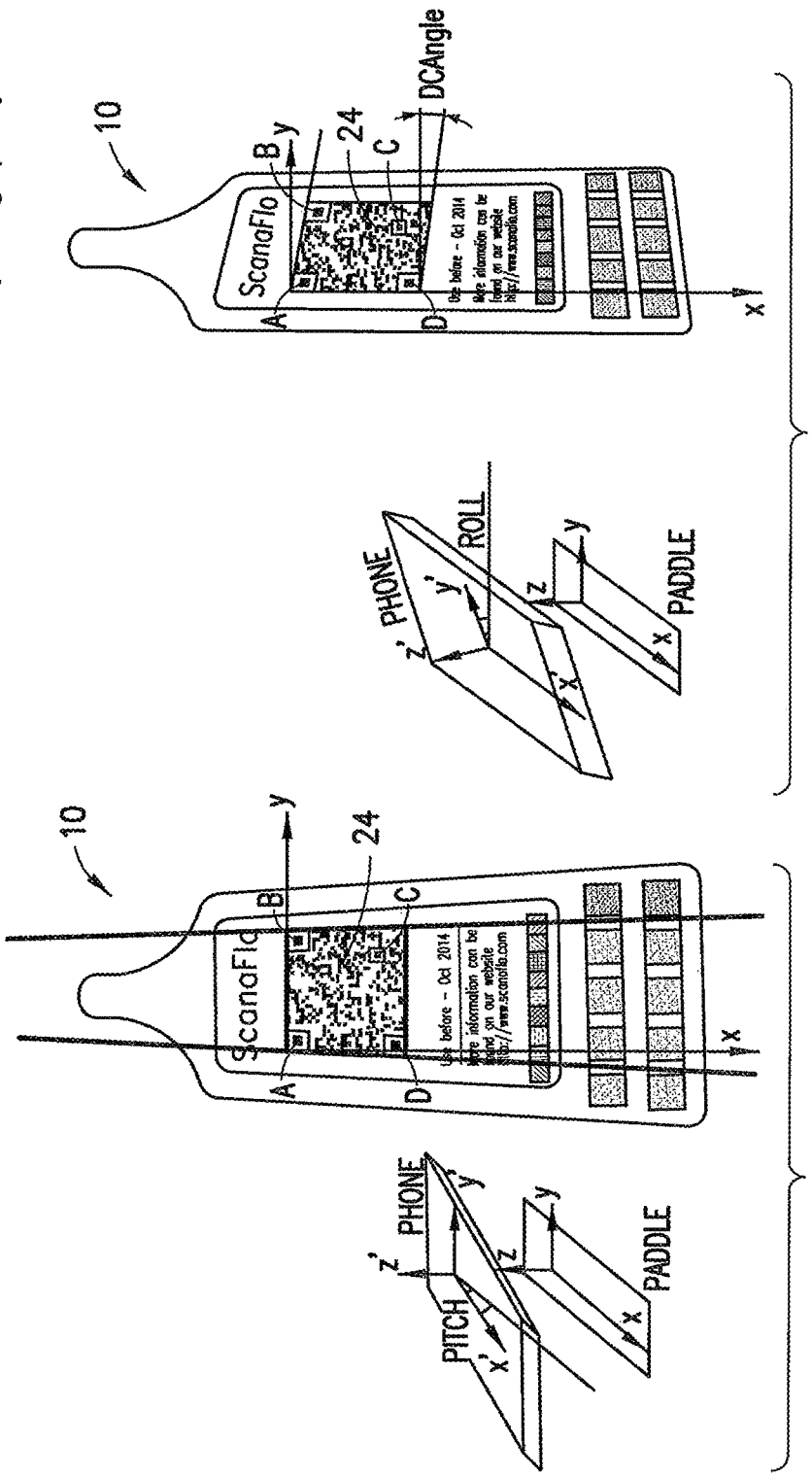

With reference to FIG. 6C, the pitch angle (rotation around Y axis) is approximated by the difference of length between AB and DC projections on axis Y'.

$$\text{Pitch approximation}=abs(Dy-Cy)/abs(Ay-By)$$

$$\text{Pitch correction}=(abs(Dy-Cy)/abs(Ay-By))^3,$$

With reference to FIG. 6D, the roll angle (rotation around X axis) is approximated by the angle between axis Y' and AB or DC segments $$DCAngle=a\tan((Cx-Dx)/(Cy-Dy));$$

The composite correction for both roll and yaw is calculated as:

$$AngFact=\sin(DCAngle)+\sin(yawAngle);$$

The coordinates of the CTP 22 are calculated by applying the following corrections to points T1 ... Tn defined in FIG. 6A to obtain its transformation TA.

$$TAy=\text{round}(Tiy*Yscale);$$

$$TAx=\text{round}(Tix*Xscale-AngFact*TAy);$$

The coordinates of the RCB 28 can be calculated using the same equations, thereby providing a theoretic location of the RCB 28 on the digital image.

Removing CTP noise and CTP Color Correction

Figure 7A:
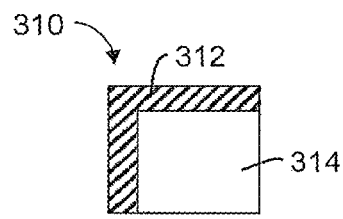
FIGS. 7A-7C are schematic representations of magnified views of color test pads including background artifacts, as identified by the geometric correction calculations of the method of FIG. 4.
Figure 7B:
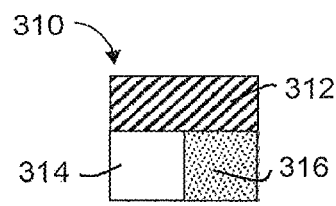
Figure 7C:
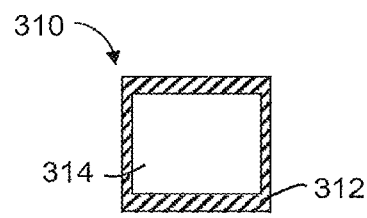

With continued reference to FIG. 4, the CTP image identified by the geometric calculations may not be perfect for various reasons. Therefore, once the CTP and RCB sub-images are identified and extracted by the geometric corrections, processes are implemented to remove CTP noise and to correct the colors 220 of the digital image to accurately reflect the coloration under standard lighting conditions. It is understood, however, that the calculated theoretic positions of the CTP and RCB, and resulting extracted sub-images, may not be accurate and align exactly with the RCP and CTP, for a variety of reasons. With reference to FIGS. 7A-7C, background artifacts 312, from the housing of the diagnostic instrument 10, may incorrectly be included within the CTP sub-image 310 identified by the geometric correction calculations, described above. The background artifacts 312 are adjacent to or surround the actual CTP image 314. As shown in FIG. 7A, background artifacts 312 are present at the left and top of the CTP sub-image 310. FIG. 7B has a large inclusion of a background artifact 312 on top and a second background artifact 316 to the right of the actual CTP image 314. FIG. 7C includes a smaller marginal background artifact 312 surrounding the actual CTP region 314. The background artifacts 312, 316 may be removed by applying a local image correction, in which spatial guard bands are placed around and just within the boundary of the actual CTP image 314. Background artifacts 312, 314 outside of the region enclosed by the guard bands are removed from the CTP sub-image. The more uniform color patch (e.g. the actual CTP image 314) within the guard band is then filtered and optimized to improve image quality.

With reference to FIG. 8, due to the length and inclination of the RCB sub-image 318 extracted from the digital image of the diagnostic instrument 10, the RCB 28 is also typically not accurately identified by the geometric correction calculations. For example, the RCB sub-image 318 may include background lines 320 of noise on top and bottom of the actual RCB image 322, as shown in FIG. 8. Accordingly, an additional step of removing the background lines 320 from the sub-image 318 to accurately identify the RCB 28 is required. This operation is performed by applying a variance operator line by line over the RCB sub-image 318. A longitudinal line across the RCB sub-image 318 with a low variance is not part of the RCB 28 and can be deleted. However, lines running across the actual RCB image 322 would have a high and well known variance. Thus, such high variance lines are not filtered out and are presumed to capture the actual RCB image 322.

Additional image imperfections including noise from the camera sensor, artifacts caused by changing lighting conditions, imperfections of the samples themselves, variations in the CTP chemical reactions, or any combination thereof may also be present in the actual CTP and RCB images 314, 322, even after the background artifacts 312, 316 and background lines 320 are removed. These imperfections may be removed by filtering and color correction. However, the challenge in filtering noise in medical applications is to avoid tampering with the raw data. This is particularly true in the colorspace where classic signal processing methods, such as linear filtering, might contaminate or distort samples and create questionable results. For example, a single red pixel averaged over a white area introduces low level pink that that could be misinterpreted as a test result. The Nitrate CTP is a good example where the slightest detection of pink corresponds to a positive result. Therefore, the filtering method of the present invention is based on a sorting operation that does not modify the raw data and does not introduce colors into existing points, even at infinitesimal levels. Additionally, the quality of the identified CTP region is further improved by conditionally rejecting anomalous color points, which fall far outside of the nominally uniform color across the test panel. Such conditional rejection of outlier points presents a significant improvement in reducing error without altering raw data.

In view of these challenges, in one embodiment, a median filter, such as median filters available for use with MATLAB data analysis software, developed by MathWorks, Inc., can be applied to the actual CTP and RCB images 314, 320 after the background artifacts are removed. Median filters have the advantage of reducing pollution of CTP and RCB by border points not already rejected by the guard bands, providing an elegant solution to an optimal value without modifying the raw data. Applying a median filter to the actual CTP and RCB images (e.g. the camera captured CTP and RCB images) provides a dominant camera-captured CTP color and a dominant camera-captured RCB color. More specifically, the median filter is applied in a line wise direction and then in a column wise direction.

Due to potential variability in lighting conditions under which the digital image is captured, the camera-captured CTP color must be color corrected prior to comparison with the MICC to calibrate the digital image to the MICC colorspace. It is noted that since the digital image of the diagnostic instrument captures both the RCB and CTP under the same lighting conditions, the digital image of the RCB reflects the same noise and bias conditions as the CTP. Therefore, the present invention recognizes that the RCB can serve as a calibration reference to color correct the color averaged CTP value.

In one embodiment, a color correction value is determined by identifying a white color sample of the RCB. A color correction factor is determined by identifying any colors, other than white, present in the camera-captured white color sample of the RCB. The correction factor is applied to the camera-captured CTP color using a white balancing algorithm, as is known in the art. For example, white balancing algorithms for use in MATLAB by Jeny Rajan, available at https://sites.google.com/site/jenyrajan/, may be used in connection with the present invention. White balancing algorithms are effective for color correcting red, green, blue images, such as the digital image of the diagnostic instrument.

Alternatively, and in a preferred and non-limiting embodiment, a color correction algorithm uses additional reference samples from the RCB to calculate both a black and white correction factor and a color correction factor for the digital image. Inherent to the invented method, the colors of each of the squares in the RCB (Cyan, Magenta, Yellow, Key (black), Gray, White, Red, Green, and Blue) are known under standard lighting (e.g. D65) conditions. The color values for the RCB under standard lighting conditions are referred to as the ReferenceRCB (RefRCB) values. These known standard color values are compared to values obtained from the actual RCB image 322, referred to as the camera-captured RCB (CCRCB), acquired according the process described above. Having two data sets, the CCRCB and the RefRCB, it is possible to construct an inverse matrix that transforms the CCRCB into RefRCB. An example of solution for deriving the inverse matrix and for correcting the color of the CTP based on the derived inverse matrix, includes the following:

1. correct the image by adjusting the luminance of the squares with the gamma factor
2. $L_{out} = A \cdot L_{out}^{gamma}$
3. This is for B&W luminance, which represents the bulk of the correction
4. correct the RGB bias balancing the three colors with another gamma factor
5. $a_{out} = B \cdot a_{out}^{gamma1}$
6. This is for color adjustments, typically a and b and Lab
7. The CMY values are used for validation Once the Gamma factors (A, gamma, B, gamma1) are derived, the correction is applied to the dominant camera-captured CTP color to bring the CTP color into the MICC colorspace.

Figure 9:
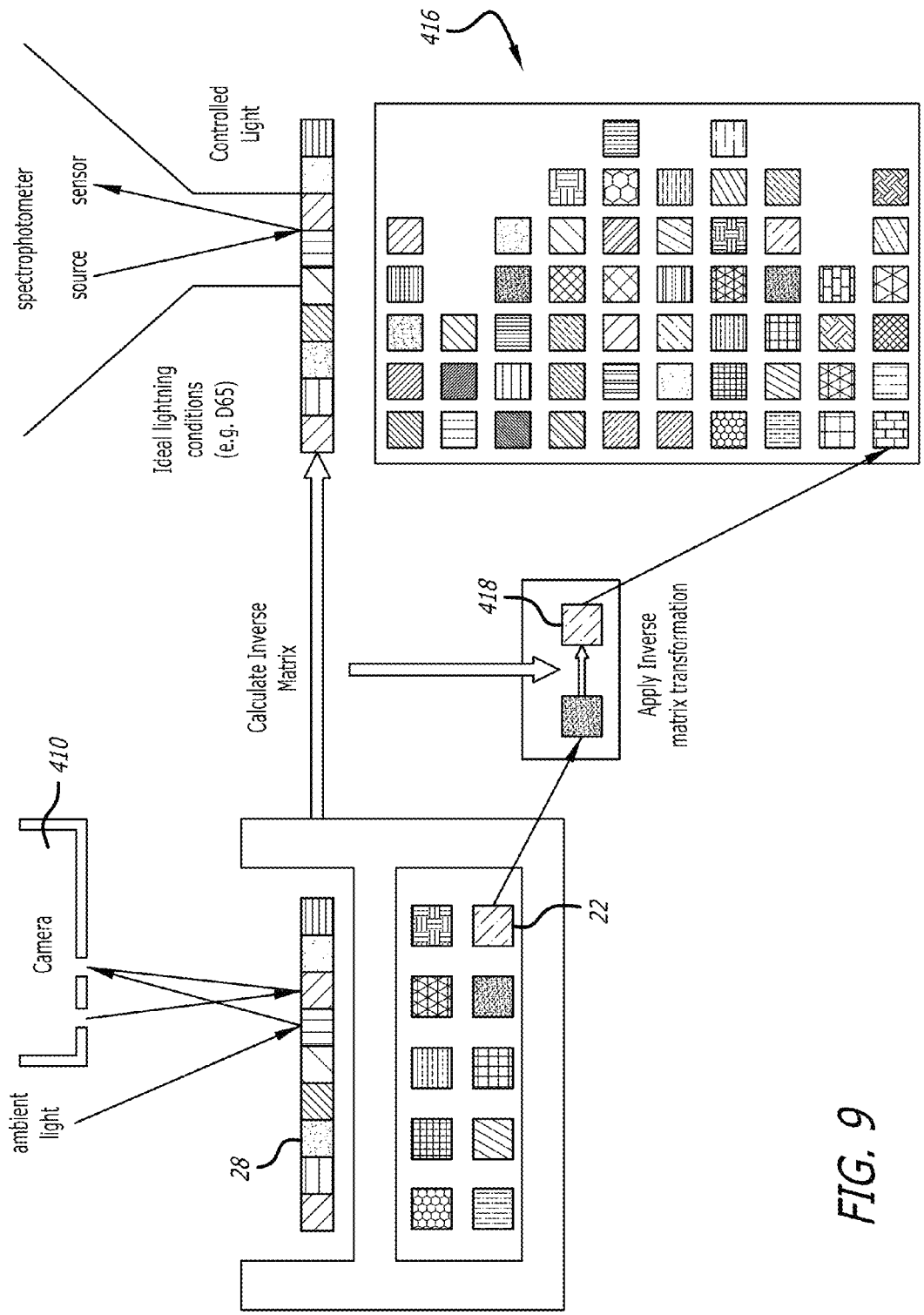
FIG. 9 is a schematic view of the process for color correcting a digital image of the chemical test pads, according to the principles of the present invention.

A schematic representation of the above described color correction process is depicted in FIG. 9. As shown in FIG. 9, the digital image of the diagnostic instrument 10 including the CTP 22 and RCB 28 is obtained using a camera 410 of the portable electronic device under various real known or unknown lighting conditions. This is the CCRCB. The digital image of the RCB 28 is compared to known color values for the RCB 28 obtained under standard or ideal lighting conditions using a spectrophotometer 412. This image is referred to as the RefRCB. The comparison between the CCRCB and RefRCB is used to create an inverse matrix 414 for mapping the CCRCB onto the RefRCB. The inverse matrix 414 is applied to the camera-captured CTP color to transform the camera captured CTP color into a color in the same colorspace as the MICC 416. Once the CTP is transformed to obtain a color corrected CTP color 418, the color corrected CTP can be compared with the MICC since both colors are presented in the same color space. In this way, the digital image of the diagnostic instrument is effectively calibrated with the MICC 416, even though the digital image was obtained under real or unknown lighting conditions.

Compare CTP to their corresponding MICC

As previously described, MICC for a number of different types of CTP arrangements may be stored on computer-readable media included on or associated with the portable electronic device. When the method described in this invention validates the UID in FIG. 4, it also selects the adequate MICC to interpret the paddle. More specifically, the validation process uses the identification information included on the UID of the diagnostic instrument being tested to select the correct MICC to interpret results of a specific test. The validation process effectively prevents a user from using the wrong diagnostic instrument or incorrect MICC, even when several families of diagnostic instrument products have a similar appearance or CTP arrangement. The color corrected CTP color is compared with color values from the corresponding MICC to determine the analyte concentration of the sample solution. The measured color is compared to the MICC values by an interpolation process.

Figure 10:
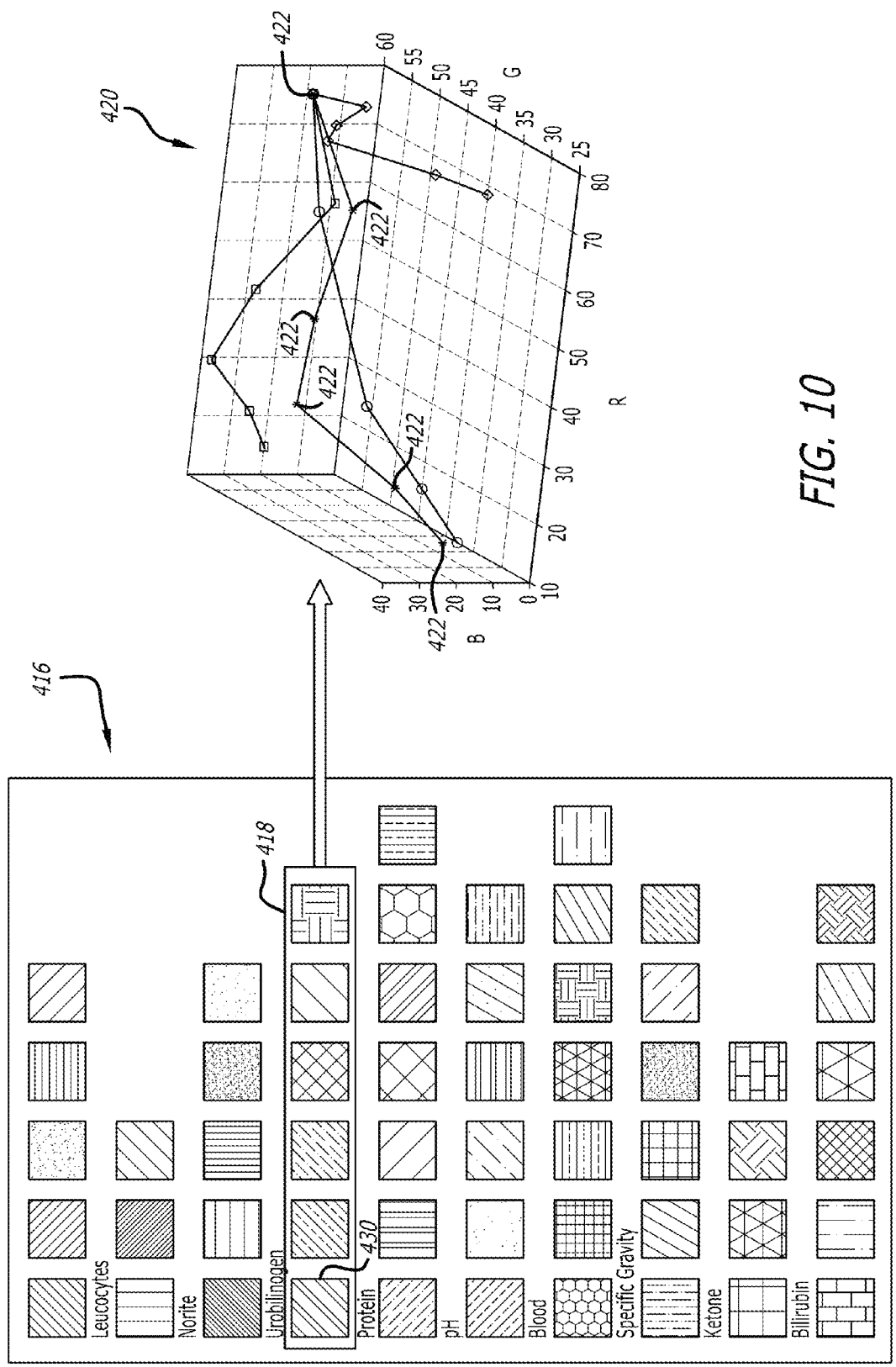
FIG. 10 is a schematic representation indicating that color samples from a Manufacturing Interpretation Color Chart are mapped in the Red-Green-Blue (RGB) colorspace.
Figure 11:
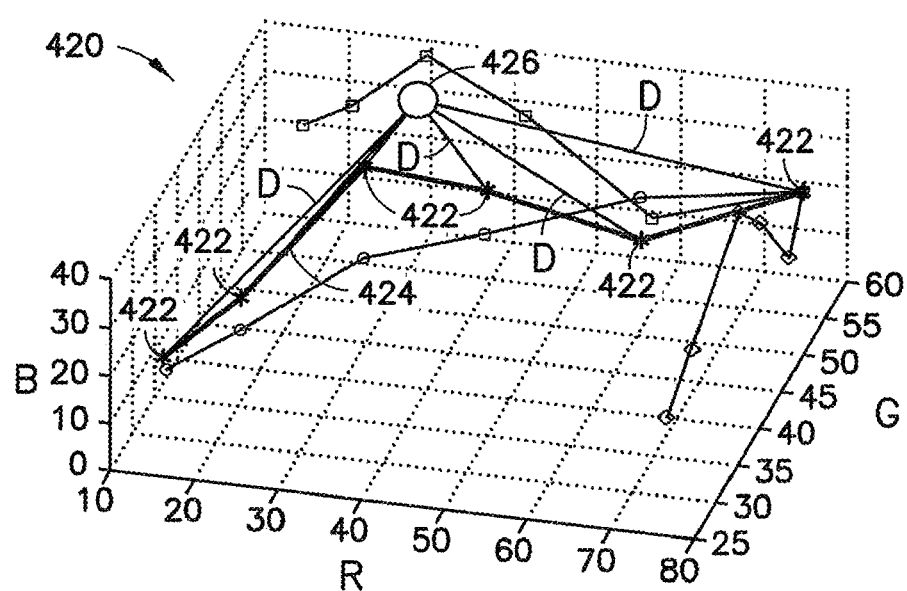
FIG. 11 is a schematic view of the RGB colorspace of FIG. 10, including the color samples from the MICC and a corrected test medium color.

Interpolation of test results using the MICC could be performed in at least two ways. With reference to FIGS. 10 and 11, the first and simplest method, which is employed in imaging processes employed in the prior art, is assessment of the distance in the color space between the color corrected CTP color and MICC values. A schematic drawing depicting such interpolation is depicted in FIGS. 10 and 11. As shown in FIG. 10, the MICC 416 for a particular CTP (e.g. a set 318 of color values representing the color change for various analyte concentrations) is represented in the RGB color space 420, as a series of discrete points 422, corresponding to MICC 416 color samples. As shown in FIG. 10, the discrete points 422 are connected by a solid trajectory line 424. With reference to FIG. 11, the color corrected CTP color 426 is also included in the colorspace 420. The method calculates the distance D between the color corrected CTP color 426 and each of the discrete points 422. The nearest discrete point 422 is thereby identified. The test result for the CTP color is reported as the analyte concentration of the closet discrete point.

Figure 12A:
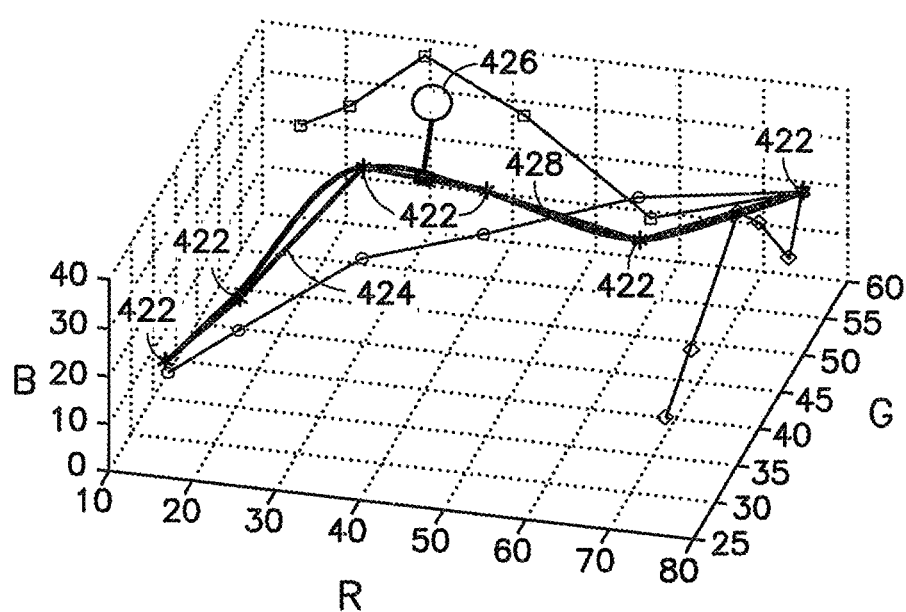
FIG. 12A is a schematic view of the RGB colorspace including a color trajectory derived from the MICC color samples and a corrected test medium color.
Figure 12B:
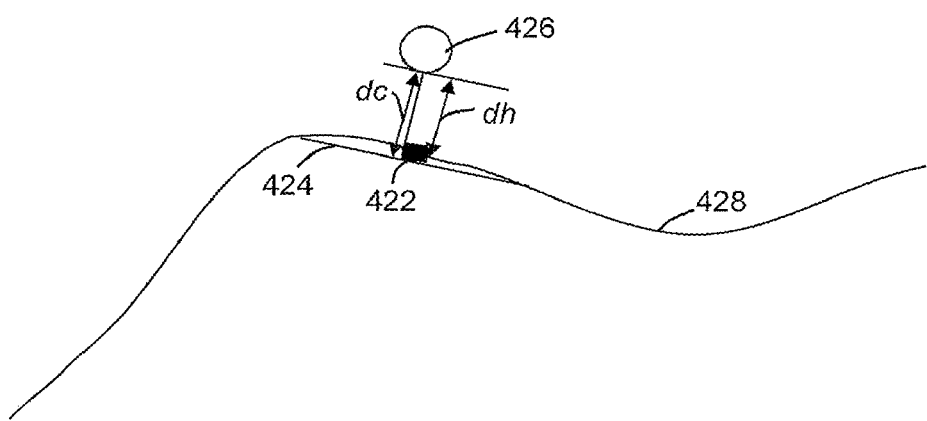
FIG. 12B is a magnified schematic view of the color trajectory of FIG. 12A.

With reference to FIGS. 12A and 12B, a second preferred method, introduces an additional metric by using the shortest distance dh between the color corrected CTP color 426 and an interpolated color trajectory 428 derived from the discrete points 422. The distance dh may be used in two simultaneous ways. First, a color trajectory function may be derived by applying polynomial interpolation. The shortest perpendicular distance dh between the color corrected CTP color 426 and the interpolated color trajectory 428 is used to calculate the predicted concentration. Secondly, if the length dh of the perpendicular to the interpolated color trajectory 428 is larger than a predetermined value, then the measurement is rejected as suspect. Conversely, if dh is less than a given predetermined value, the measurement may be assumed to be trustworthy. In addition, the concentration may be further refined by proportional interpolation between the two closest discrete points 422 to the color corrected CTP 426 to further improve quantitative accuracy, using known algorithms. In an alternative embodiment, the perpendicular distance dc between the color corrected CTP color 426 and the trajectory line 424 connecting the discrete points 422, defined as the chord between the discrete points 420, also yields a valuable and simplified method for calculating concentration, which is an improvement over currently available methods.

In either case, the color corrected portion of the digital image including the CTP is proportionally mapped on to the precisely interpolated polynomial, or chordal, fit in the chosen color space (e.g. the red-green-blue (RGB) colorspace). Although the above discussion refers to the RGB color space, it will be appreciated by those well versed in the art that any color space may be used (e.g. CMYK, CIE, Pantone, Munsell, etc.).

Beneficially the above method is quite tolerant of non-linearities, and does not require a unitary relationship with any human visual properties, making its numerical value and interpretation independent of the color vision of the observer, ambient lighting when the digital image was taken, residual metamerism, or indeed most commonly encountered errors, for which calibration and compensation did not formerly exist.

Once a plurality of analyte concentrations are calculated, the test results may be provided to a user. Additionally, the complete set of test results may be interpreted in combination as a medically-coherent set, to more specifically determine a patient condition.

Test Results and Titrations of CTP

Figure 13:
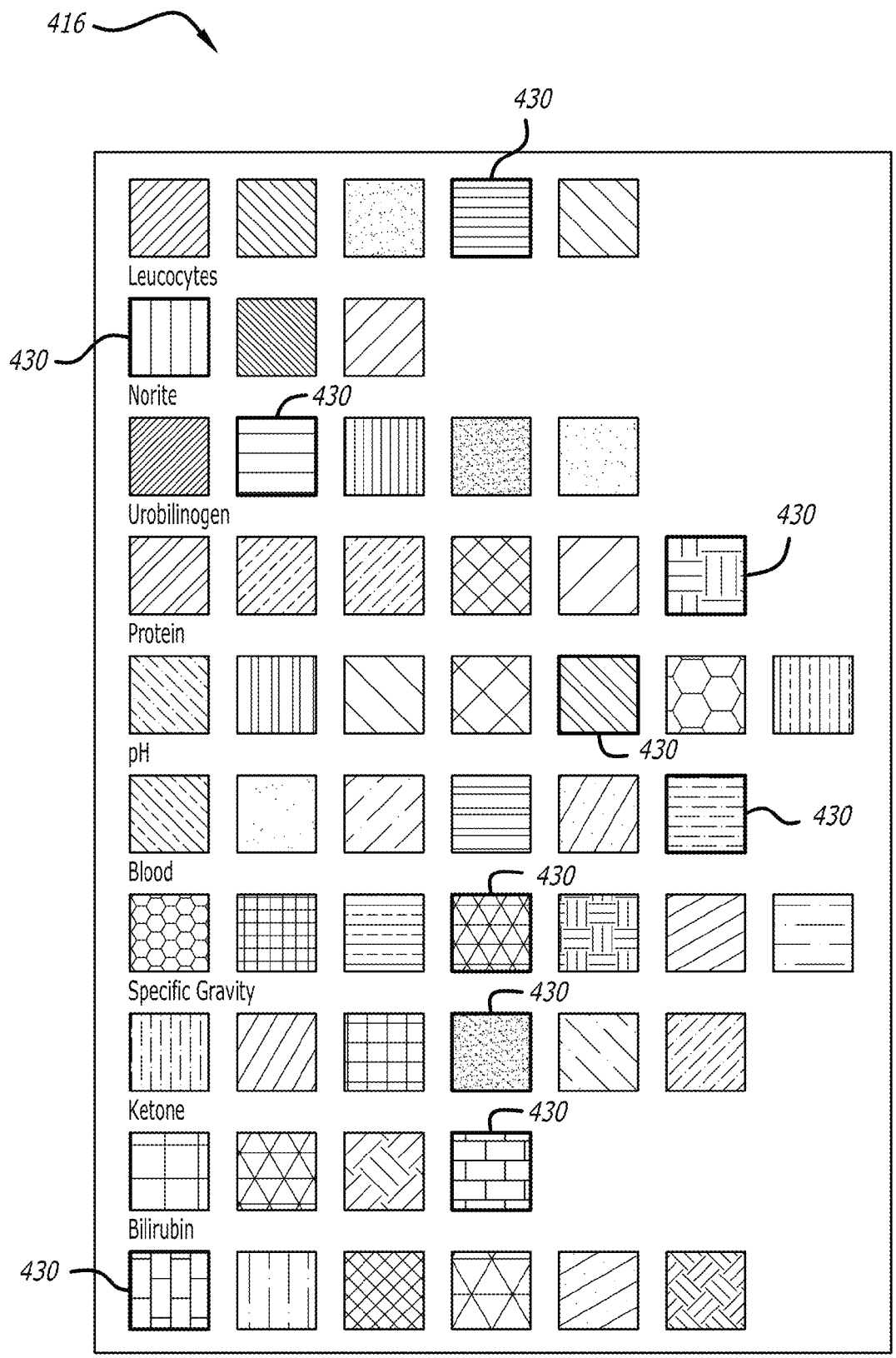
FIG. 13 is a photographic representation of a Manufacturing Interpretation Color Chart with test results identified.

Test results are presented to a user by a visual display connected to or associated with the portable electronic device. A simple way to visualize test results is to present the user with an image of the MICC and draw a border around the closest MICC color samples. A possible visual depiction of an MICC 416 showing selected color samples 430, corresponding to the identified test results, is depicted in FIG. 13.

Another way to visualize test results is to print the analyte being tested for and the concentration or titration (e.g. normal, positive, very positive, etc.) in a list or table. The list or table can be presented on the visual display of the device, as shown below in Table 1 The correspondence between these the titrations and the colors read by the algorithm is encoded in a look-up table linking the MICC to the titrations. Typical values provided are – negative, trace, small (+), moderate (++), large (+++).

TABLE 1

| Leukocytes | Moderate |
|---|---|
| Nitrate | Negative |
| Uro-bilinogen | 1 |
| ... | |

Interpretation of the Result

The test results may be further analyzed to provide the user with information about a possible patient condition. In a simple form, the interpretation may include displaying additional facts about the patient condition and possible treatment options. In further embodiments, the method may consider results of two or more separate tests to provide additional information about a patient condition. For example, an indication that the patient has both high leukocytes levels and high nitrites suggests a urinary tract infection (UTI).

In cases where this interpretation might lead to ambiguity, the software may engage in a user dialogue by asking additional contextual questions to the user in order to resolve ambiguities and provide an approximate interpretation in accordance with the medical state of the art. These additional questions are typically implemented as a decision tree, a method well known in the state of the art. For example if the diagnostic instrument 10 identifies a high level of bilirubin, the decision tree function of the software may ask the user for additional information about medications being taken to detect whether the user is experiencing an allergic reaction to a particular medication. Exemplary decision trees for use with the diagnostic instrument of the present invention are depicted in FIGS. 14 and 15.

Secure Embodiment for Verification of Unused Diagnostic Instrument

In a further non-limiting embodiment of the invented method, the diagnostic instrument may be examined prior to use to ensure that it is undamaged and suitable for use. More specifically, storage, conditioning, transport and the exposure of the diagnostic instrument to contaminants like air, could damage the diagnostic instrument, making it unreliable in use. It is noted that exposure to containments may render the diagnostic instrument unsuitable for use even if the diagnostic instrument has not yet reached its anticipated expiration date. Accordingly, steps are needed to ensure that the diagnostic instrument is capable of producing accurate results.

Figure 16:
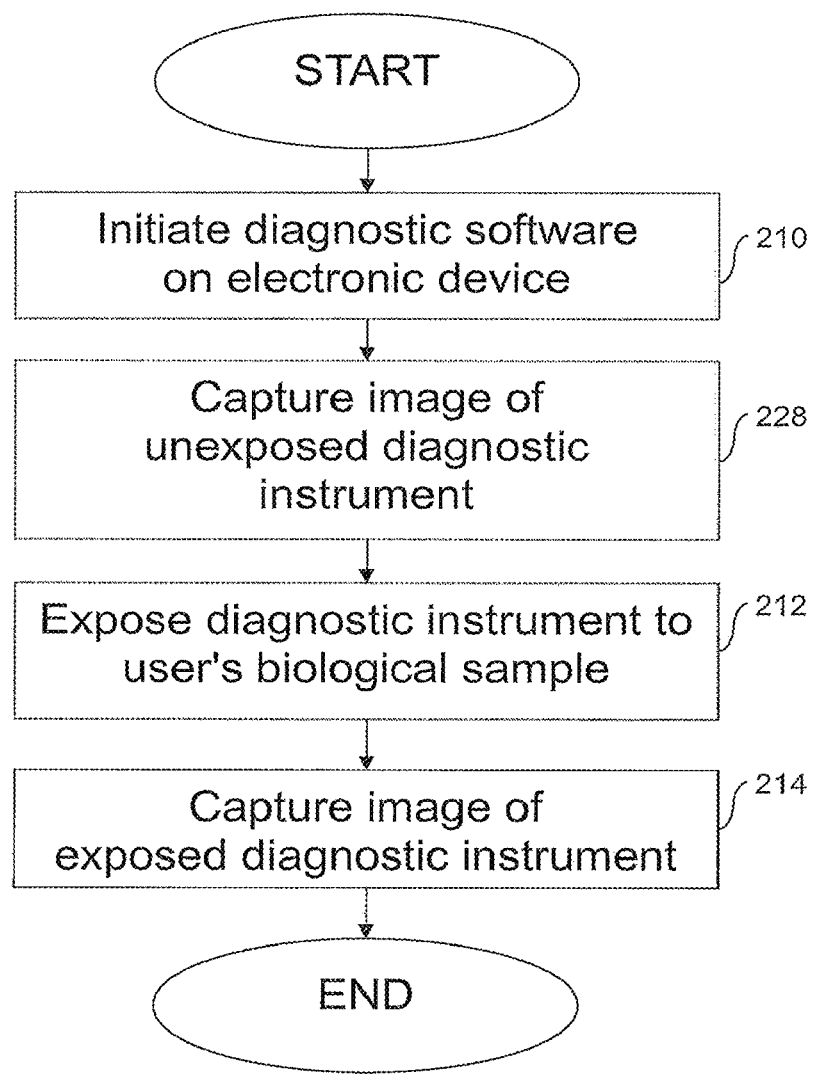
FIG. 16 is a flow chart of an embodiment of a method for capturing an image of a diagnostic instrument, according to the principles of the invention.
Figure 17:
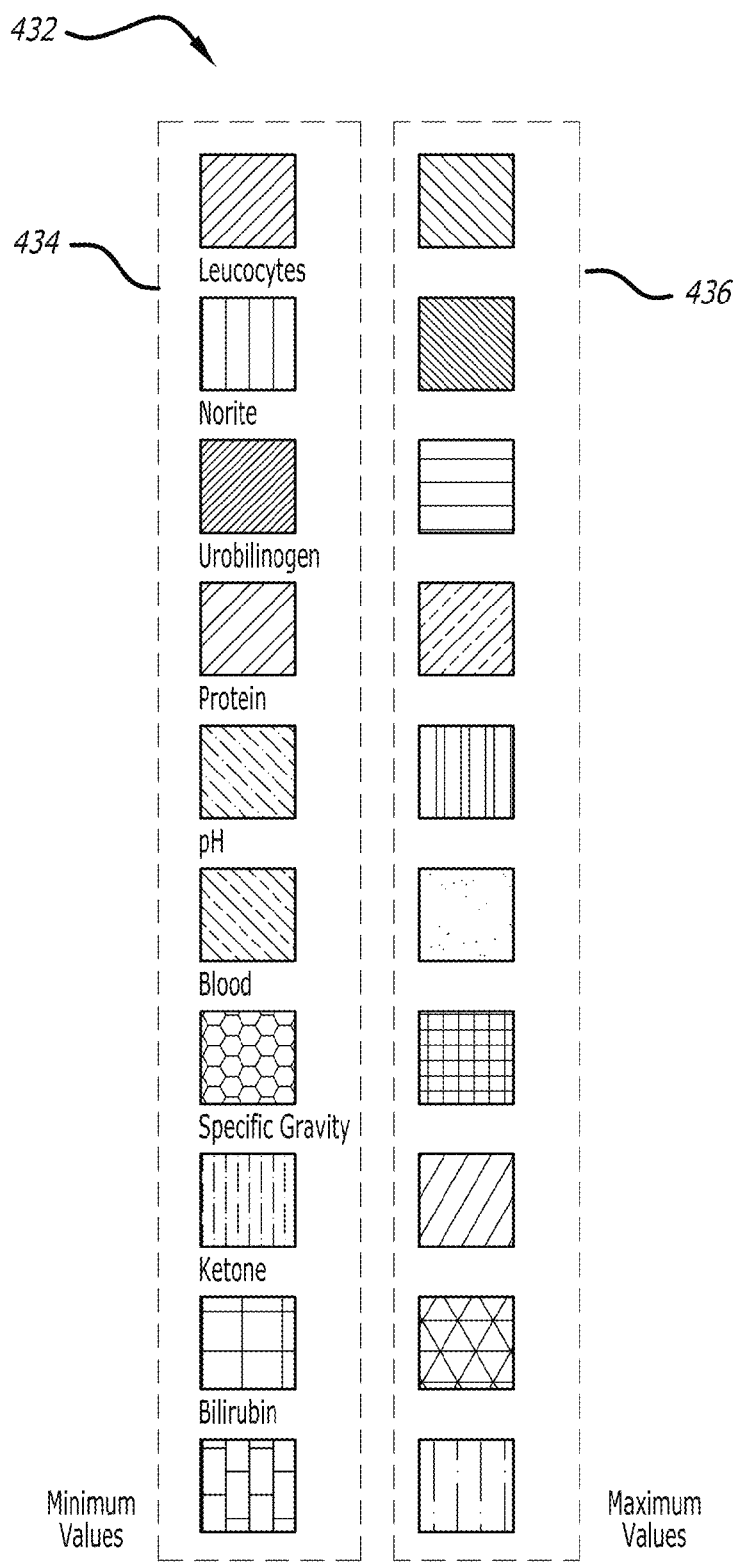
FIG. 17 is a schematic view of a table depicting minimum and maximum color change values for a plurality of chemical test pads, for use in verification of a diagnostic instrument, according to the principles of the present invention.

As shown in the exemplary embodiment of FIG. 16, in this embodiment, the user captures an image of the diagnostic instrument prior to exposing the diagnostic instrument to the biological sample 228. The other steps are equivalent to the method for capturing a digital image depicted in FIG. 3. The step of capturing the image of the unexposed diagnostic instrument prior to exposing the instrument to the fluid sample is used to verify that the initial (e.g. unused) colors of the CTP, prior to coming into contact with the fluid sample, are within a normal range. More specifically, the appearance of the unused CTP is compared to expected original values by using the algorithms for color comparison described above, in connection with comparing the color-corrected CTP color to the MICC. However, rather than comparing the color corrected CTP colors to the MICC, the color corrected CTP values are compared against a Security Table built during the risk and quality management process for the diagnostic instrument. An exemplary Security Table 432 is depicted in FIG. 17. The Table 432 includes a minimum possible subset 434 of colors for each unused CTP. If the color corrected CTP color for the unused CTP differs from the color samples of the table 432 by more than a predetermined amount, the diagnostic instrument is rejected as defective. More specifically, the Security Table defines the tolerances of acceptable unexposed diagnostic instrument colors. Any deviation from the expected tolerance is rejected. Notice also that table 432 reflects colorimetric values for dry samples, which might appear lighter color than the wet values processed with exposed samples and reported in the MICC.

Similarly, after the diagnostic instrument is exposed to the fluid sample and before performing additional image analysis on the diagnostic instrument, a digital image of the diagnostic instrument could be compared against a set of colors 436 corresponding to the maximum possible CTP color change. The method of comparing the color change of the CTP with the maximum color change values is the same as the above described comparison processes. If the color change of the CTP is found to exceed the theoretical maximum possible color change, the results are rejected as invalid. In that case, no further image processing needs be performed and the diagnostic instrument should be discarded as defective.

The above described methods may be implemented on a variety of electronic and computing devices and systems, including portable electronic devices and/or server computers, wherein these computing devices include appropriate processing mechanisms and computer readable media for storing and executing the computer readable instructions, such as programming instructions, code, and the like.

Figure 18:
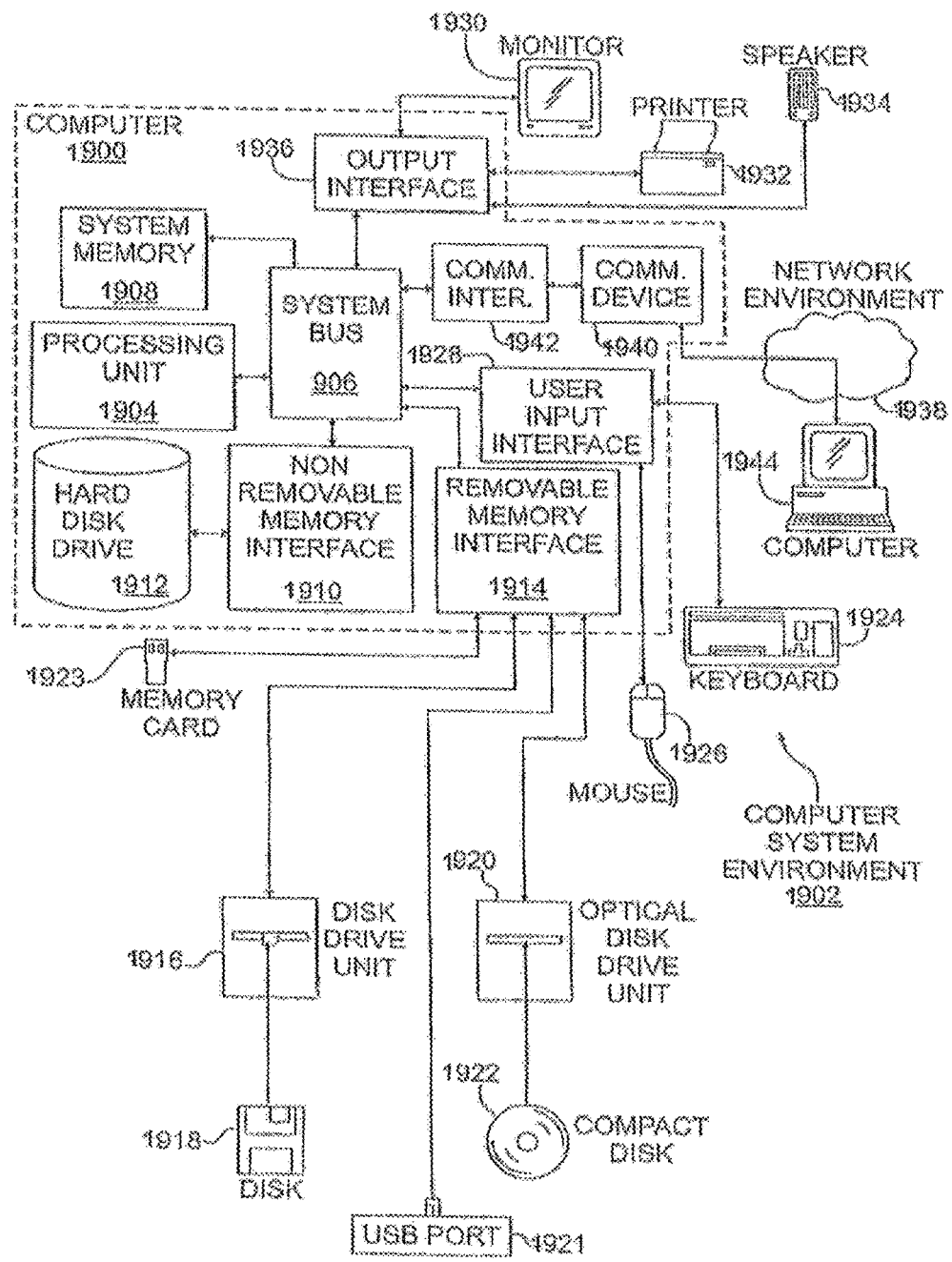
FIG. 18 is a schematic diagram of a computer network infrastructure according to the prior art.

As shown in FIG. 18, personal computers 1900, 1944, in a computing system environment 1902 are provided. This computing system environment 1902 may include, but is not limited to, at least one computer 1900 having certain components for appropriate operation, execution of code, and creation and communication of data. For example, the computer 1900 includes a processing unit 1904 (typically referred to as a central processing unit or CPU) that serves to execute computer based instructions received in the appropriate data form and format. Further, this processing unit 1904 may be in the form of multiple processors executing code in series, in parallel, or in any other manner for appropriate implementation of the computer-based instructions.

In order to facilitate appropriate data communication and processing information between the various components of the computer 1900, a system bus 1906 is utilized. The system bus 1906 may be any of several types of bus structures, including a memory bus or memory controller, a peripheral bus, or a local bus using any of a variety of bus architectures. In particular, the system bus 1906 facilitates data and information communication between the various components (whether internal or external to the computer 1900) through a variety of interfaces, as discussed hereinafter.

The computer 1900 may include a variety of discrete computer-readable media components. For example, this computer-readable media may include any media that can be accessed by the computer 1900, such as volatile media, non-volatile media, removable media, non-removable media, etc. As a further example, this computer-readable media may include computer storage media, such as media implemented in any method or technology for storage of information, such as computer-readable instructions, data structures, program modules, or other data, random access memory (RAM), read only memory (ROM), electrically erasable programmable read only memory (EEPROM), flash memory, or other memory technology, CD-ROM, digital versatile disks (DVDs), or other optical disk storage, magnetic cassettes, magnetic tape, magnetic disk storage, or other magnetic storage devices, or any other medium which can be used to store the desired information and which can be accessed by the computer 1900. Further, this computer-readable media may include communications media, such as computer-readable instructions, data structures, program modules, or other data in other transport mechanisms and include any information delivery media, wired media (such as a wired network and a direct-wired connection), and wireless media. Computer-readable media may include all machine-readable media with the sole exception of transitory, propagating signals. Of course, combinations of any of the above should also be included within the scope of computer-readable media.

The computer 1900 further includes a system memory 1908 with computer storage media in the form of volatile and non-volatile memory, such as ROM and RAM. A basic input/output system (BIOS) with appropriate computer-based routines assists in transferring information between components within the computer 1900 and is normally stored in ROM. The RAM portion of the system memory 1908 typically contains data and program modules that are immediately accessible to or presently being operated on by processing unit 1904, e.g., an operating system, application programming interfaces, application programs, program modules, program data and other instruction-based computer-readable codes.

With continued reference to FIG. 18, the computer 1900 may also include other removable or non-removable, volatile or non-volatile computer storage media products. For example, the computer 1900 may include a non-removable memory interface 1910 that communicates with and controls a hard disk drive 1912, i.e., a non-removable, non-volatile magnetic medium; and a removable, non-volatile memory interface 1914 that communicates with and controls a magnetic disk drive unit 1916 (which reads from and writes to a removable, non-volatile magnetic disk 1918), an optical disk drive unit 1920 (which reads from and writes to a removable, non-volatile optical disk 1922, such as a CD ROM), a Universal Serial Bus (USB) port 1921 for use in connection with a removable memory card, etc. However, it is envisioned that other removable or non-removable, volatile or nonvolatile computer storage media can be used in the exemplary computing system environment 1900, including, but not limited to, magnetic tape cassettes, DVDs, digital video tape, solid state RAM, solid state ROM, etc. These various removable or non-removable, volatile or non-volatile magnetic media are in communication with the processing unit 1904 and other components of the computer 1900 via the system bus 1906. The drives and their associated computer storage media discussed above and illustrated in FIG. 18 provide storage of operating systems, computer-readable instructions, application programs, data structures, program modules, program data and other instruction-based computer-readable code for the computer 1900 (whether duplicative or not of this information and data in the system memory 1908).

A user may enter commands, information, and data into the computer 1900 through certain attachable or operable input devices, such as a keyboard 1924, a mouse 1926, etc., via a user input interface 1928. Of course, a variety of such input devices may be utilized, e.g., a microphone, a trackball, a joystick, a touchpad, a touch-screen, a scanner, etc., including any arrangement that facilitates the input of data, and information to the computer 1900 from an outside source. As discussed, these and other input devices are often connected to the processing unit 1904 through the user input interface 1928 coupled to the system bus 1906, but may be connected by other interface and bus structures, such as a parallel port, game port, or a universal serial bus (USB). Still further, data and information can be presented or provided to a user in an intelligible form or format through certain output devices, such as a monitor 1930 (to visually display this information and data in electronic form), a printer 1932 (to physically display this information and data in print form), a speaker 1934 (to audibly present this information and data in audible form), etc. All of these devices are in communication with the computer 1900 through an output interface 1936 coupled to the system bus 1906. It is envisioned that any such peripheral output devices be used to provide information and data to the user.

The computer 1900 may operate in a network environment 1938 through the use of a communications device 1940, which is integral to the computer or remote therefrom. This communications device 1940 is operable by and in communication to the other components of the computer 1900 through a communications interface 1942. Using such an arrangement, the computer 1900 may connect with or otherwise communicate with one or more remote computers, such as a remote computer 1944, which may be a personal computer, a server, a router, a network personal computer, a peer device, or other common network nodes, and typically includes many or all of the components described above in connection with the computer 1900. Using appropriate communication devices 1940, e.g., a modem, a network interface or adapter, etc., the computer 1900 may operate within and communication through a local area network (LAN) and a wide area network (WAN), but may also include other networks such as a virtual private network (VPN), an office network, an enterprise network, an intranet, the Internet, etc. It will be appreciated that the network connections shown are exemplary and other means of establishing a communications link between the computers 1900, 1944 may be used.

As used herein, the computer 1900 includes or is operable to execute appropriate custom-designed or conventional software to perform and implement the processing steps of the method and system of the present invention, thereby, forming a specialized and particular computing system. Accordingly, the presently-invented method and system may include one or more computers 1900 or similar computing devices having a computer-readable storage medium capable of storing computer-readable program code or instructions that cause the processing unit 1902 to execute, configure or otherwise implement the methods, processes, and transformational data manipulations discussed hereinafter in connection with the present invention. Still further, the computer 1900 may be in the form of a personal computer, a personal digital assistant, a portable computer, a laptop, a palmtop, a mobile device, a mobile telephone, a server, or any other type of computing device having the necessary processing hardware to appropriately process data to effectively implement the presently-invented computer-implemented method and system.

Methods and electronic devices for performing color-based reaction testing of biological materials have been disclosed. The method includes capturing and interpreting digital images of an unexposed and later exposed paddle at various delay times within an automatically calibrated environment. The test paddle includes a unique identification mechanism (UID), a Reference Color Bar (RCB) providing samples of standardized colors for image color calibration, compensation and corrections for such, and several test-specific sequences of Chemical Test Pads (CTP). The method further includes locating the paddle in the image, extracting the UID and validating the paddle, extracting the RCB and locating the plurality of CTP in each image. The method further reduces image noise in the CTP and calibrates the image automatically according to lighting measurements performed on the RCB. The method further determines several distances between the CTP and its possible trajectory in the color space described by the Manufacturer Interpretation Color Chart (MICC). These distances determine the test results, which are conventionally the nearest color pad in the MICC. Additionally, the invention interpolates concentrations between those indicated by the discrete test pads and reports the level of uncertainty of each measurement. The method shows these results in graphical or quantified mode. The method further interprets these results based on medically documented relationships between readings and conditions, mapping test results to potential causes.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A computer-implemented method for determining a relative position on a diagnostic instrument, the method comprising:
   capturing a digital image of at least a portion of the diagnostic instrument, which has been exposed to a biological sample, the diagnostic instrument comprising at least one test medium containing a reagent, which changes color in the presence of particular analytes in the biological sample;
   scanning the digital image to identify the position of a predetermined region on the diagnostic instrument;
   identifying the at least one test medium on the digital image based at least in part on the position of the predetermined region; and
   determining a test result by comparing the color of the at least one test medium to a set of possible test medium colors corresponding to predetermined analyte concentrations to determine an analyte concentration of the biological sample being tested.

2. The method of claim 1, wherein the diagnostic instrument further comprises a plurality of test media arranged in a plurality of test specific sequences.

3. The method of claim 1, wherein the identifying step further comprises:
   determining geometric corrections for the digital image based at least in part on the position of the predetermined region, the geometric corrections comprising an angle of rotation of the diagnostic instrument about at least one of the following: the x-axis, the y-axis, the z-axis, or any combination thereof, and,
   calculating the position of the at least one test medium based at least partially on the position of the identification label and the geometric corrections.

4. The method of claim 1, wherein the predetermined region comprises an identification label including or associated with identification information about the diagnostic instrument.

5. The method of claim 4, wherein the identification information includes at least one of the following: the manufacture date of the diagnostic instrument; the expiration date of the diagnostic instrument; the analytes tested for by the instrument; identifying information about the test subject; patient condition information; or any combination thereof.

6. The method of claim 4, wherein the identification label comprises at least one of the following: a bar code, a QR code, a near-field communication tag, or any combination thereof.

7. A method for validating a diagnostic instrument comprising:
   capturing a pre-use digital image of at least a portion of the diagnostic instrument, prior to exposing the diagnostic instrument to a biological sample, the diagnostic instrument comprising at least one color reference comprising a plurality of reference samples of different colors and at least one test medium containing a reagent, which changes color in the presence of particular analytes in the biological sample;
   identifying the at least one test medium in the pre-use digital image of the diagnostic instrument;
   comparing a color of the at least one test medium to a set of possible test medium colors for reagents, which have not been exposed to an analyte; and
   determining whether the diagnostic instrument is in condition for use based at least in part on the color of the at least one test medium.

8. The method of claim 7, wherein the diagnostic instrument further comprises an identification label including or associated with identification information about the diagnostic instrument, and wherein the captured digital image of the diagnostic instrument includes at least a portion of the identification label.

9. The method of claim 8, wherein the identification label is at least one of the following: a bar code; a QR code, a near-field communication tag, or any combination thereof.

10. The method of claim 8, wherein the identification information includes at least one of the following: the manufacture date of the diagnostic instrument; the expiration date of the diagnostic instrument; the analytes tested for by the instrument; identifying information about the test subject; patient condition information; or any combination thereof.

11. The method of claim 8, wherein the determining step further comprises analyzing the portion of the pre-use digital image including the identification label to determine the identification information and determining whether the diagnostic instrument is in condition for use based, at least in part, on the identification information.

12. A diagnostic instrument for identifying a plurality of test results by testing a single patient fluid, the instrument comprising:
   an instrument housing;
   a color reference comprising a plurality of reference samples of different colors affixed to or associated with the housing for determining the test results from a digital image of the diagnostic instrument; and
   a plurality of test media affixed to the housing containing color-changing reagents, which change color in the presence of particular analytes in a biological sample.

13. The diagnostic instrument of claim 12, wherein the plurality of test media are arranged in a plurality of test specific sequences.

14. The diagnostic instrument of claim 13, wherein the instrument housing comprises a paddle having a handle and a plurality of indentations disposed on the paddle for receiving the plurality of test media.

15. The diagnostic instrument of claim 13, further comprising an identification label disposed on the instrument housing including or associated with identification information about the diagnostic instrument including at least one of the following: the manufacture date of the instrument, the expiration date of the instrument, the analytes for which the instrument tests, identifying information about the test subject, the patient conditions, or any combination thereof.

16. The diagnostic instrument of claim 15, wherein the identification label comprises at least one of the following: a bar code, a QR code, a near-field communication tag, or any combination thereof.

17. The diagnostic instrument of claim 12, wherein the plurality of test media comprise a super-hydrophobic coating for preventing fluid from dripping from the test media.

* * * * *